United States Patent
Marchand et al.

(10) Patent No.: US 10,448,944 B2
(45) Date of Patent: *Oct. 22, 2019

(54) FILAMENTARY FIXATION DEVICE

(71) Applicant: Howmedica Osteonics Corp., Mahwah, NJ (US)

(72) Inventors: José Raúl Marchand, San Juan, PR (US); Ryan E. Yearsley, Denver, CO (US); Kyle Craig Pilgeram, San Jose, CA (US)

(73) Assignee: Howmedica Osteonics Corp., Mahwah, NJ (US)

( * ) Notice: Subject to any disclaimer, the term of this patent is extended or adjusted under 35 U.S.C. 154(b) by 332 days.

This patent is subject to a terminal disclaimer.

(21) Appl. No.: 15/243,183

(22) Filed: Aug. 22, 2016

(65) Prior Publication Data

US 2016/0354079 A1    Dec. 8, 2016

Related U.S. Application Data

(63) Continuation of application No. 13/303,849, filed on Nov. 23, 2011, now Pat. No. 9,445,803.

(51) Int. Cl.
A61B 17/04    (2006.01)

(52) U.S. Cl.
CPC .... *A61B 17/0401* (2013.01); *A61B 2017/042* (2013.01); *A61B 2017/0403* (2013.01); *A61B 2017/0459* (2013.01)

(58) Field of Classification Search
CPC .......... A61B 17/0401; A61B 17/06166; A61B 2017/0403; A61B 2017/0404;
(Continued)

(56) References Cited

U.S. PATENT DOCUMENTS

| 749,624 A | 1/1904 | McCullough |
| 1,308,798 A | 7/1919 | Masland |

(Continued)

FOREIGN PATENT DOCUMENTS

| CA | 2713309 A1 | 2/2011 |
| DE | 3131496 A1 | 2/1983 |

(Continued)

OTHER PUBLICATIONS

ConMed: Linvatec: Shoulder Restoration System Y-Knot 1.3mm All Suture Anchor, © 2011 Linvatec Corporation, a subsidiary of ConMed Corporation—CBR 3057 (4 pages).

(Continued)

*Primary Examiner* — Dianne Dornbusch
(74) *Attorney, Agent, or Firm* — Lerner, David, Littenberg, Krumholz & Mentlik, LLP

(57) ABSTRACT

One embodiment of the present invention includes a filamentary fixation system including a sleeve formed of filamentary material including an interior and an exterior surface along a length defined between a first end and a second end, the sleeve having a coating adapted to allow for tissue ingrowth, and a filament formed of filamentary material including a first free end and a second free end, and a length therebetween, at least a portion of the filament positioned within the interior of the sleeve.

19 Claims, 18 Drawing Sheets

(58) Field of Classification Search
CPC .... A61B 2017/0406; A61B 2017/0408; A61B 2017/0414; A61B 2017/0417; A61B 2017/0419; A61B 2017/042; A61B 2017/0438; A61B 2017/0445; A61B 2017/06185

See application file for complete search history.

(56) References Cited

U.S. PATENT DOCUMENTS

| | | |
|---|---|---|
| 1,624,530 A | 4/1927 | Caruso |
| 2,073,903 A | 3/1937 | O'Neil |
| 2,250,434 A | 7/1941 | Dugaw |
| 2,267,925 A | 12/1941 | Johnston |
| 2,382,019 A | 8/1945 | Miller |
| 2,461,947 A | 2/1949 | Weber |
| 2,494,229 A | 1/1950 | Collison |
| 2,515,365 A | 7/1950 | Zublin |
| 2,547,571 A | 4/1951 | Ettinger |
| 2,773,672 A | 12/1956 | Holmes et al. |
| 2,808,632 A | 10/1957 | Cline |
| 2,833,284 A | 5/1958 | Springer |
| 3,384,085 A | 5/1968 | Hall |
| 3,407,889 A | 10/1968 | Hjalsten et al. |
| 3,461,875 A | 8/1969 | Hall |
| 3,554,192 A | 1/1971 | Isberner |
| 3,580,256 A | 5/1971 | Wilkinson et al. |
| 3,608,095 A | 9/1971 | Barry |
| 3,659,597 A | 5/1972 | Wolfers |
| 3,750,671 A | 8/1973 | Hedrick |
| 3,810,456 A | 5/1974 | Karman |
| 3,845,772 A | 11/1974 | Smith |
| 3,867,932 A | 2/1975 | Huene |
| 3,892,232 A | 7/1975 | Neufeld |
| 3,976,079 A | 8/1976 | Samuels et al. |
| 3,981,051 A | 9/1976 | Brumlik |
| 4,212,569 A | 7/1980 | Andersson et al. |
| 4,265,231 A | 5/1981 | Scheller, Jr. et al. |
| 4,328,839 A | 5/1982 | Lyons et al. |
| 4,483,562 A | 11/1984 | Schoolman |
| 4,489,446 A | 12/1984 | Reed |
| 4,541,423 A | 9/1985 | Barber |
| 4,594,033 A | 6/1986 | Peetz et al. |
| 4,605,347 A | 8/1986 | Jodock et al. |
| 4,608,972 A | 9/1986 | Small |
| 4,611,515 A | 9/1986 | Marbourg, Jr. |
| 4,635,738 A | 1/1987 | Schillinger et al. |
| 4,646,738 A | 3/1987 | Trott |
| 4,706,659 A | 11/1987 | Matthews et al. |
| 4,728,231 A | 3/1988 | Kunimori et al. |
| 4,741,330 A | 5/1988 | Hayhurst |
| 4,748,872 A | 6/1988 | Brown |
| 4,751,922 A | 6/1988 | DiPietropolo |
| 4,781,182 A | 11/1988 | Purnell et al. |
| 4,823,780 A | 4/1989 | Odensten et al. |
| 4,842,451 A | 6/1989 | Dugger |
| 4,863,471 A | 9/1989 | Mansat |
| 4,872,451 A | 10/1989 | Moore et al. |
| 4,946,462 A | 8/1990 | Watanabe |
| 5,002,546 A | 3/1991 | Romano |
| 5,007,911 A | 4/1991 | Baker |
| 5,021,059 A | 6/1991 | Kensey et al. |
| 5,030,219 A | 7/1991 | Matsen, III et al. |
| 5,037,422 A | 8/1991 | Hayhurst et al. |
| 5,037,423 A | 8/1991 | Kenna |
| 5,061,277 A | 10/1991 | Carpentier et al. |
| 5,064,431 A * | 11/1991 | Gilbertson ............ A61F 2/2445 623/2.37 |
| 5,122,134 A | 6/1992 | Borzone et al. |
| 5,123,914 A | 6/1992 | Cope |
| 5,133,720 A | 7/1992 | Greenberg |
| 5,139,520 A | 8/1992 | Rosenberg |
| 5,141,520 A | 8/1992 | Goble et al. |
| 5,163,940 A | 11/1992 | Bourque |
| 5,165,494 A | 11/1992 | Barr |
| 5,186,268 A | 2/1993 | Clegg |
| 5,190,548 A | 3/1993 | Davis |
| 5,203,595 A | 4/1993 | Borzone et al. |
| 5,203,787 A | 4/1993 | Noblitt et al. |
| RE34,293 E | 6/1993 | Goble et al. |
| 5,234,435 A | 8/1993 | Seagrave, Jr. |
| 5,259,846 A | 11/1993 | Granger et al. |
| 5,269,785 A | 12/1993 | Bonutti |
| 5,269,809 A | 12/1993 | Hayhurst et al. |
| 5,273,380 A | 12/1993 | Musacchia |
| 5,300,077 A | 4/1994 | Howell |
| 5,314,429 A | 5/1994 | Goble |
| 5,320,115 A | 6/1994 | Kenna |
| 5,320,626 A | 6/1994 | Schmieding |
| 5,324,308 A | 6/1994 | Pierce |
| 5,330,468 A | 7/1994 | Burkhart |
| 5,342,376 A | 8/1994 | Ruff |
| 5,350,383 A | 9/1994 | Schmieding et al. |
| RE34,762 E | 10/1994 | Goble et al. |
| 5,374,269 A | 12/1994 | Rosenberg |
| 5,380,334 A | 1/1995 | Torrie et al. |
| 5,385,567 A | 1/1995 | Goble |
| 5,391,170 A | 2/1995 | McGuire et al. |
| 5,391,171 A | 2/1995 | Schmieding |
| RE34,871 E | 3/1995 | McGuire et al. |
| 5,395,188 A | 3/1995 | Bailey et al. |
| 5,403,317 A | 4/1995 | Bonutti |
| 5,403,348 A | 4/1995 | Bonutti |
| 5,405,359 A | 4/1995 | Pierce |
| 5,409,494 A | 4/1995 | Morgan |
| 5,417,691 A | 5/1995 | Hayhurst |
| 5,423,824 A | 6/1995 | Akerfeldt et al. |
| 5,423,860 A | 6/1995 | Lizardi et al. |
| 5,437,630 A | 8/1995 | Daniel et al. |
| 5,437,675 A | 8/1995 | Wilson |
| 5,437,677 A | 8/1995 | Shearer et al. |
| 5,441,502 A | 8/1995 | Bartlett |
| 5,443,482 A | 8/1995 | Stone et al. |
| 5,458,604 A | 10/1995 | Schmieding |
| 5,464,407 A | 11/1995 | McGuire |
| 5,464,425 A | 11/1995 | Skiba |
| 5,464,426 A | 11/1995 | Bonutti |
| 5,466,243 A | 11/1995 | Schmieding et al. |
| 5,472,452 A | 12/1995 | Trott |
| 5,486,197 A | 1/1996 | Le et al. |
| 5,488,761 A | 2/1996 | Leone |
| 5,496,348 A | 3/1996 | Bonutti |
| 5,505,736 A | 4/1996 | Reimels et al. |
| 5,520,693 A | 5/1996 | McGuire et al. |
| 5,520,700 A | 5/1996 | Beyar et al. |
| 5,522,846 A | 6/1996 | Bonutti |
| 5,527,316 A | 6/1996 | Stone et al. |
| 5,527,343 A | 6/1996 | Bonutti |
| 5,529,580 A | 6/1996 | Kusunoki et al. |
| 5,531,759 A | 7/1996 | Kensey et al. |
| 5,534,012 A | 7/1996 | Bonutti |
| 5,540,703 A | 7/1996 | Barker, Jr. et al. |
| 5,545,178 A * | 8/1996 | Kensey ............ A61B 17/0057 604/15 |
| 5,548,862 A | 8/1996 | Curtis |
| 5,569,269 A | 10/1996 | Hart et al. |
| 5,569,306 A | 10/1996 | Thal |
| 5,570,706 A | 11/1996 | Howell |
| 5,571,111 A | 11/1996 | Aboczky |
| 5,573,542 A | 11/1996 | Stevens |
| 5,575,819 A | 11/1996 | Amis |
| 5,584,617 A | 12/1996 | Houser |
| 5,584,695 A | 12/1996 | Lal Sachdeva et al. |
| 5,584,835 A | 12/1996 | Greenfield |
| 5,601,550 A | 2/1997 | Esser |
| 5,601,557 A | 2/1997 | Hayhurst |
| 5,601,561 A | 2/1997 | Terry et al. |
| 5,618,314 A | 4/1997 | Harwin et al. |
| 5,645,545 A | 7/1997 | Bryant |
| 5,645,589 A | 7/1997 | Li |
| 5,647,874 A | 7/1997 | Hayhurst |
| 5,649,963 A | 7/1997 | McDevitt |
| 5,658,289 A | 8/1997 | Boucher et al. |
| 5,658,313 A | 8/1997 | Thal |
| 5,662,658 A | 9/1997 | Wenstrom, Jr. |

(56) References Cited

U.S. PATENT DOCUMENTS

| | | |
|---|---|---|
| 5,664,914 A | 9/1997 | Taniguchi |
| 5,665,110 A | 9/1997 | Chervitz et al. |
| 5,665,111 A | 9/1997 | Ray et al. |
| 5,665,112 A | 9/1997 | Thal |
| 5,667,509 A | 9/1997 | Westin |
| 5,671,695 A | 9/1997 | Schroeder |
| 5,674,279 A | 10/1997 | Wright et al. |
| 5,681,315 A | 10/1997 | Szabo |
| 5,681,320 A | 10/1997 | McGuire |
| 5,681,352 A | 10/1997 | Clancy, III et al. |
| 5,683,401 A | 11/1997 | Schmieding et al. |
| 5,683,418 A | 11/1997 | Luscombe et al. |
| 5,683,419 A | 11/1997 | Thal |
| 5,690,676 A | 11/1997 | DiPoto et al. |
| 5,690,677 A | 11/1997 | Schmieding et al. |
| 5,695,513 A | 12/1997 | Johnson et al. |
| 5,699,657 A | 12/1997 | Paulson |
| 5,702,397 A | 12/1997 | Goble et al. |
| 5,707,374 A | 1/1998 | Schmidt |
| 5,709,708 A | 1/1998 | Thal |
| 5,713,905 A | 2/1998 | Goble et al. |
| 5,716,397 A * | 2/1998 | Myers ............... A61F 2/2445 606/1 |
| 5,718,717 A | 2/1998 | Bonutti |
| 5,720,765 A | 2/1998 | Thal |
| 5,725,530 A | 3/1998 | Popken |
| 5,725,541 A | 3/1998 | Anspach, III et al. |
| 5,725,557 A | 3/1998 | Gatturna et al. |
| 5,728,136 A | 3/1998 | Thal |
| 5,732,606 A | 3/1998 | Chiang |
| 5,733,306 A | 3/1998 | Bonutti |
| 5,733,307 A | 3/1998 | Dinsdale |
| 5,749,899 A | 5/1998 | Bardin et al. |
| 5,755,724 A | 5/1998 | Yoon |
| 5,755,731 A | 5/1998 | Grinberg |
| 5,759,185 A | 6/1998 | Grinberg |
| 5,766,221 A | 6/1998 | Benderev et al. |
| 5,782,862 A | 7/1998 | Bonutti |
| 5,782,864 A | 7/1998 | Lizardi |
| 5,782,866 A | 7/1998 | Wenstrom, Jr. |
| 5,788,699 A | 8/1998 | Bobst et al. |
| 5,797,918 A | 8/1998 | McGuire et al. |
| 5,810,825 A | 9/1998 | Huebner |
| 5,814,056 A | 9/1998 | Prosst et al. |
| 5,820,464 A | 10/1998 | Parlato |
| 5,836,953 A | 11/1998 | Yoon |
| 5,851,208 A | 12/1998 | Trott |
| 5,885,294 A | 3/1999 | Pedlick et al. |
| 5,888,034 A | 3/1999 | Greenberg |
| 5,891,168 A | 4/1999 | Thal |
| 5,895,179 A | 4/1999 | Gschwend et al. |
| 5,897,574 A | 4/1999 | Bonutti |
| 5,906,626 A | 5/1999 | Carrillo |
| 5,908,423 A | 6/1999 | Kashuba et al. |
| 5,921,986 A | 7/1999 | Bonutti |
| 5,928,244 A | 7/1999 | Tovey et al. |
| 5,941,139 A | 8/1999 | Vodehnal |
| 5,941,883 A | 8/1999 | Sklar |
| 5,947,659 A | 9/1999 | Mays |
| 5,948,002 A | 9/1999 | Bonutti |
| 5,951,559 A | 9/1999 | Burkhart |
| 5,954,747 A | 9/1999 | Clark |
| 5,961,538 A * | 10/1999 | Pedlick ............... A61B 17/0401 606/104 |
| 5,968,078 A | 10/1999 | Grotz |
| 5,970,697 A | 10/1999 | Jacobs et al. |
| 5,980,539 A | 11/1999 | Kontos |
| 5,980,558 A | 11/1999 | Wiley |
| 5,980,559 A | 11/1999 | Bonutti |
| 5,989,252 A * | 11/1999 | Fumex ............... A61B 17/0401 606/232 |
| 5,993,451 A | 11/1999 | Burkhart |
| 5,997,541 A | 12/1999 | Schenk |
| 6,007,566 A | 12/1999 | Wenstrom, Jr. |
| 6,007,567 A | 12/1999 | Bonutti |
| 6,010,515 A | 1/2000 | Swain et al. |
| 6,010,525 A | 1/2000 | Bonutti et al. |
| 6,019,767 A | 2/2000 | Howell |
| 6,024,758 A | 2/2000 | Thal |
| 6,030,406 A | 2/2000 | Davis et al. |
| 6,045,574 A | 4/2000 | Thal |
| 6,053,922 A | 4/2000 | Krause et al. |
| 6,068,642 A | 5/2000 | Johnson et al. |
| 6,077,292 A | 6/2000 | Bonutti |
| 6,083,244 A | 7/2000 | Lubbers et al. |
| 6,083,522 A | 7/2000 | Chu et al. |
| 6,120,511 A | 9/2000 | Chan |
| 6,143,017 A | 11/2000 | Thal |
| 6,146,385 A | 11/2000 | Torrie et al. |
| 6,152,949 A | 11/2000 | Bonutti |
| 6,156,039 A | 12/2000 | Thal |
| 6,156,056 A | 12/2000 | Kearns et al. |
| 6,159,234 A | 12/2000 | Bonutti et al. |
| 6,183,461 B1 | 2/2001 | Matsuura et al. |
| 6,187,011 B1 | 2/2001 | Torrie |
| 6,189,422 B1 | 2/2001 | Stihl |
| 6,210,415 B1 | 4/2001 | Bester |
| 6,224,608 B1 | 5/2001 | Ciccolella et al. |
| 6,245,081 B1 | 6/2001 | Bowman et al. |
| 6,254,604 B1 | 7/2001 | Howell |
| 6,258,093 B1 | 7/2001 | Edwards et al. |
| 6,270,501 B1 | 8/2001 | Freiberg et al. |
| 6,296,659 B1 | 10/2001 | Foerster |
| 6,306,138 B1 | 10/2001 | Clark et al. |
| 6,306,159 B1 | 10/2001 | Schwartz et al. |
| 6,312,438 B1 | 11/2001 | Adams |
| 6,343,482 B1 | 2/2002 | Endo et al. |
| 6,352,538 B2 | 3/2002 | McGuire et al. |
| 6,358,253 B1 | 3/2002 | Torrie et al. |
| 6,364,886 B1 | 4/2002 | Sklar |
| 6,383,188 B2 | 5/2002 | Kuslich et al. |
| 6,402,781 B1 * | 6/2002 | Langberg ............... A61F 2/2451 623/1.11 |
| 6,416,517 B2 | 7/2002 | Harder et al. |
| 6,419,678 B1 | 7/2002 | Asfora |
| 6,419,684 B1 | 7/2002 | Heisler et al. |
| 6,431,801 B2 | 8/2002 | Vasudeva et al. |
| 6,436,100 B1 | 8/2002 | Berger |
| 6,436,124 B1 | 8/2002 | Anderson et al. |
| 6,440,138 B1 | 8/2002 | Reiley et al. |
| 6,440,141 B1 | 8/2002 | Philippon |
| 6,447,518 B1 | 9/2002 | Krause et al. |
| 6,464,713 B2 | 10/2002 | Bonutti |
| 6,474,425 B1 | 11/2002 | Truax et al. |
| 6,475,230 B1 * | 11/2002 | Bonutti ............... A61B 17/0487 606/232 |
| 6,478,800 B1 | 11/2002 | Fraser et al. |
| 6,485,504 B1 | 11/2002 | Johnson et al. |
| 6,494,272 B1 | 12/2002 | Eppink et al. |
| 6,500,195 B2 | 12/2002 | Bonutti |
| RE37,963 E | 1/2003 | Thal |
| 6,508,830 B2 | 1/2003 | Steiner |
| 6,511,498 B1 * | 1/2003 | Fumex ............... A61B 17/0401 606/232 |
| 6,517,578 B2 | 2/2003 | Hein |
| 6,544,281 B2 | 4/2003 | ElAttrache et al. |
| 6,558,386 B1 | 5/2003 | Cragg |
| 6,558,390 B2 | 5/2003 | Cragg |
| 6,569,187 B1 | 5/2003 | Bonutti et al. |
| 6,572,635 B1 | 6/2003 | Bonutti |
| 6,575,979 B1 | 6/2003 | Cragg |
| 6,599,310 B2 | 7/2003 | Leung et al. |
| 6,610,080 B2 | 8/2003 | Morgan |
| 6,635,073 B2 | 10/2003 | Bonutti |
| 6,638,279 B2 | 10/2003 | Bonutti |
| 6,638,283 B2 | 10/2003 | Thal |
| 6,641,597 B2 | 11/2003 | Burkhart et al. |
| 6,652,450 B2 * | 11/2003 | Neisz ............... A61B 17/0401 600/30 |
| 6,660,023 B2 | 12/2003 | McDevitt et al. |
| 6,712,822 B2 | 3/2004 | Re et al. |
| 6,716,234 B2 | 4/2004 | Grafton et al. |
| 6,730,092 B2 | 5/2004 | Songer |
| 6,740,090 B1 | 5/2004 | Cragg et al. |

(56) References Cited

U.S. PATENT DOCUMENTS

| | | |
|---|---|---|
| 6,746,451 B2 | 6/2004 | Middleton et al. |
| 6,773,450 B2 | 8/2004 | Leung et al. |
| 6,780,188 B2 | 8/2004 | Clark et al. |
| 6,783,533 B2 | 8/2004 | Green et al. |
| 6,790,210 B1 | 9/2004 | Cragg et al. |
| 6,805,697 B1 | 10/2004 | Helm et al. |
| 6,824,552 B2 | 11/2004 | Robison et al. |
| 6,830,570 B1 | 12/2004 | Frey et al. |
| 6,848,152 B2 | 2/2005 | Genova et al. |
| 6,863,672 B2 | 3/2005 | Reiley et al. |
| 6,874,978 B2 | 4/2005 | Gongola |
| 6,878,150 B1 | 4/2005 | McGuire et al. |
| 6,887,259 B2 | 5/2005 | Lizardi |
| 6,893,445 B1 | 5/2005 | Revie et al. |
| 6,899,716 B2 | 5/2005 | Cragg |
| 6,921,403 B2 | 7/2005 | Cragg et al. |
| 6,923,811 B1 | 8/2005 | Carl et al. |
| 6,923,814 B1 | 8/2005 | Hildebrand et al. |
| 6,936,052 B2 | 8/2005 | Gellman et al. |
| 6,955,683 B2 | 10/2005 | Bonutti |
| 6,960,214 B2 | 11/2005 | Burkinshaw |
| 6,984,241 B2 | 1/2006 | Lubbers et al. |
| 6,991,636 B2 | 1/2006 | Rose |
| 6,994,719 B2 | 2/2006 | Grafton |
| 6,994,725 B1 | 2/2006 | Goble |
| 6,995,683 B2 | 2/2006 | Smithson et al. |
| 7,008,431 B2 | 3/2006 | Simonson |
| 7,018,144 B2 | 3/2006 | Sasagawa et al. |
| 7,025,770 B2 | 4/2006 | McGuire et al. |
| 7,029,479 B2 | 4/2006 | Tallarida et al. |
| 7,029,490 B2 | 4/2006 | Grafton et al. |
| 7,041,107 B2 | 5/2006 | Pohjonen et al. |
| 7,048,754 B2 | 5/2006 | Martin et al. |
| 7,056,331 B2 | 6/2006 | Kaplan et al. |
| 7,060,073 B2 | 6/2006 | Frey et al. |
| 7,067,132 B2 | 6/2006 | Grabstein et al. |
| 7,077,863 B2 | 7/2006 | Schmieding et al. |
| 7,087,058 B2 | 8/2006 | Cragg |
| 7,087,073 B2 | 8/2006 | Bonutti |
| 7,204,839 B2 | 4/2007 | Dreyfuss et al. |
| 7,217,279 B2 | 5/2007 | Reese |
| 7,217,290 B2 | 5/2007 | Bonutti |
| 7,225,512 B2 | 6/2007 | Genova et al. |
| 7,235,091 B2 | 6/2007 | Thornes |
| 7,241,297 B2 | 7/2007 | Shaolian et al. |
| 7,258,692 B2 | 8/2007 | Thelen et al. |
| 7,261,016 B2 | 8/2007 | Miller |
| 7,285,124 B2 | 10/2007 | Foerster |
| 7,309,338 B2 | 12/2007 | Cragg |
| 7,326,215 B2 | 2/2008 | Myers et al. |
| 7,331,263 B2 | 2/2008 | Erickson et al. |
| 7,371,253 B2 | 5/2008 | Leung et al. |
| 7,381,213 B2 | 6/2008 | Lizardi |
| 7,488,322 B2 | 2/2009 | Brunnett et al. |
| 7,488,329 B2 | 2/2009 | Thelen et al. |
| 7,494,490 B2 | 2/2009 | Justin |
| 7,500,977 B2 | 3/2009 | Assell et al. |
| 7,503,920 B2 | 3/2009 | Siegal |
| 7,520,898 B2 | 4/2009 | Re et al. |
| 7,563,266 B2 | 7/2009 | Camino et al. |
| 7,578,836 B2 | 8/2009 | Justin et al. |
| 7,585,300 B2 | 9/2009 | Cha |
| 7,601,155 B2 | 10/2009 | Petersen |
| 7,601,165 B2 | 10/2009 | Stone |
| 7,604,636 B1 | 10/2009 | Walters et al. |
| 7,608,098 B1 | 10/2009 | Stone et al. |
| 7,611,521 B2 | 11/2009 | Lubbers et al. |
| 7,621,912 B2 | 11/2009 | Harms et al. |
| 7,621,940 B2 | 11/2009 | Harms et al. |
| 7,624,487 B2 | 12/2009 | Trull et al. |
| 7,651,509 B2 | 1/2010 | Bojarski et al. |
| 7,651,515 B2 | 1/2010 | Mack et al. |
| 7,658,751 B2 | 2/2010 | Stone et al. |
| 7,666,189 B2 | 2/2010 | Gerber et al. |
| 7,678,134 B2 | 3/2010 | Schmieding et al. |
| 7,749,250 B2 | 7/2010 | Stone et al. |
| 7,776,049 B1 | 8/2010 | Curran et al. |
| 7,803,173 B2 | 9/2010 | Burkhart et al. |
| 7,857,829 B2 | 12/2010 | Kaplan et al. |
| 7,857,830 B2 | 12/2010 | Stone et al. |
| 7,875,057 B2 | 1/2011 | Cook et al. |
| 7,875,058 B2 | 1/2011 | Holmes, Jr. |
| 7,879,037 B2 | 2/2011 | Brunnett et al. |
| 7,892,235 B2 | 2/2011 | Ellis |
| 7,892,256 B2 | 2/2011 | Grafton et al. |
| 7,901,431 B2 | 3/2011 | Shumas |
| 7,905,903 B2 | 3/2011 | Stone et al. |
| 7,905,904 B2 * | 3/2011 | Stone ............... A61B 17/0401 606/232 |
| 7,909,547 B2 | 3/2011 | Jordan et al. |
| 7,909,851 B2 | 3/2011 | Stone et al. |
| 7,913,365 B2 | 3/2011 | Genova et al. |
| 7,914,539 B2 | 3/2011 | Stone et al. |
| 7,918,874 B2 | 4/2011 | Siegal |
| 7,959,650 B2 | 6/2011 | Kaiser et al. |
| 7,963,967 B1 | 6/2011 | Woods |
| 7,981,117 B2 | 7/2011 | Newton et al. |
| 7,981,140 B2 | 7/2011 | Burkhart |
| 7,993,369 B2 | 8/2011 | Dreyfuss |
| 7,996,967 B2 | 8/2011 | Genova et al. |
| 7,996,968 B2 | 8/2011 | Genova et al. |
| 8,002,733 B2 | 8/2011 | Kraft et al. |
| 8,011,072 B2 | 9/2011 | Genova et al. |
| 8,015,678 B2 | 9/2011 | Genova et al. |
| 8,020,263 B2 | 9/2011 | Genova et al. |
| 8,028,387 B2 | 10/2011 | Genova et al. |
| 8,028,388 B2 | 10/2011 | Genova et al. |
| 8,032,996 B2 | 10/2011 | Trull et al. |
| 8,043,253 B2 | 10/2011 | Kraft et al. |
| 8,057,500 B2 | 11/2011 | Mitusina |
| 8,070,750 B2 | 12/2011 | Wenstrom, Jr. et al. |
| 8,083,770 B2 | 12/2011 | Ruff et al. |
| 8,088,130 B2 | 1/2012 | Kaiser et al. |
| 8,100,940 B2 | 1/2012 | Leung et al. |
| 8,109,700 B2 | 2/2012 | Jordan et al. |
| 8,114,088 B2 | 2/2012 | Miller |
| 8,118,834 B1 | 2/2012 | Goraltchouk et al. |
| 8,118,836 B2 | 2/2012 | Denham et al. |
| 8,123,750 B2 | 2/2012 | Norton et al. |
| 8,128,640 B2 | 3/2012 | Harris et al. |
| 8,128,658 B2 | 3/2012 | Kaiser et al. |
| 8,128,669 B2 | 3/2012 | Bonutti |
| 8,133,231 B2 | 3/2012 | Martinek et al. |
| 8,137,382 B2 | 3/2012 | Denham et al. |
| 8,147,514 B2 | 4/2012 | Bonutti |
| 8,162,997 B2 | 4/2012 | Struhl |
| 8,172,846 B2 | 5/2012 | Brunnett et al. |
| 8,216,273 B1 | 7/2012 | Goraltchouk et al. |
| 8,231,654 B2 | 7/2012 | Kaiser et al. |
| 8,231,674 B2 | 7/2012 | Albertorio et al. |
| 8,241,305 B2 | 8/2012 | Stone |
| 8,246,652 B2 | 8/2012 | Ruff |
| 8,267,959 B2 | 9/2012 | Fallman |
| 8,273,106 B2 | 9/2012 | Stone et al. |
| 8,292,921 B2 | 10/2012 | Stone et al. |
| 8,298,262 B2 | 10/2012 | Stone et al. |
| 8,303,604 B2 | 11/2012 | Stone et al. |
| 8,312,942 B2 | 11/2012 | Ho et al. |
| 8,317,825 B2 | 11/2012 | Stone |
| 8,337,525 B2 | 12/2012 | Stone et al. |
| 8,343,187 B2 | 1/2013 | Lamson et al. |
| 8,361,113 B2 | 1/2013 | Stone et al. |
| 8,366,713 B2 | 2/2013 | Long et al. |
| 8,394,129 B2 | 3/2013 | Morgenstern Lopez et al. |
| 8,398,678 B2 | 3/2013 | Baker et al. |
| 8,409,253 B2 | 4/2013 | Stone et al. |
| 8,439,976 B2 | 5/2013 | Albertorio et al. |
| 8,460,338 B2 | 6/2013 | Goraltchouk et al. |
| 8,460,379 B2 | 6/2013 | Albertorio et al. |
| 8,469,998 B2 | 6/2013 | Sojka et al. |
| 8,512,340 B2 | 8/2013 | Easley et al. |
| 8,518,087 B2 | 8/2013 | Lopez et al. |
| 8,556,911 B2 | 10/2013 | Mehta et al. |
| 8,562,645 B2 | 10/2013 | Stone et al. |

(56) References Cited

U.S. PATENT DOCUMENTS

| | | |
|---|---|---|
| 8,591,578 B2 | 11/2013 | Albertorio et al. |
| 8,597,333 B2 | 12/2013 | Morgenstern Lopez et al. |
| 8,623,051 B2 | 1/2014 | Bojarski et al. |
| 8,663,324 B2 | 3/2014 | Schmieding et al. |
| 8,801,800 B2 | 8/2014 | Bagga et al. |
| 8,814,905 B2 | 8/2014 | Sengun et al. |
| 8,821,543 B2 | 9/2014 | Hernandez et al. |
| 8,821,544 B2 | 9/2014 | Sengun et al. |
| 8,821,545 B2 | 9/2014 | Sengun |
| 8,936,620 B2 | 1/2015 | Kaiser et al. |
| 9,072,530 B2 | 7/2015 | Mehta et al. |
| 9,370,350 B2 | 6/2016 | Norton |
| 2001/0027320 A1 | 10/2001 | Sasso |
| 2002/0019635 A1 | 2/2002 | Wenstrom et al. |
| 2002/0052649 A1* | 5/2002 | Greenhalgh ......... A61F 2/0063 623/1.35 |
| 2002/0087166 A1 | 7/2002 | Brock et al. |
| 2002/0183758 A1 | 12/2002 | Middleton et al. |
| 2002/0188301 A1 | 12/2002 | Dallara et al. |
| 2003/0032961 A1 | 2/2003 | Pelo et al. |
| 2003/0176919 A1 | 9/2003 | Schmieding |
| 2003/0195565 A1 | 10/2003 | Bonutti |
| 2003/0220646 A1 | 11/2003 | Thelen et al. |
| 2003/0233098 A1 | 12/2003 | Markworth |
| 2004/0010264 A1 | 1/2004 | Acker et al. |
| 2004/0010287 A1 | 1/2004 | Bonutti |
| 2004/0030346 A1 | 2/2004 | Frey et al. |
| 2004/0049194 A1 | 3/2004 | Harvie et al. |
| 2004/0060409 A1 | 4/2004 | Leung et al. |
| 2004/0073227 A1 | 4/2004 | Dreyfuss et al. |
| 2004/0073306 A1 | 4/2004 | Eichhorn et al. |
| 2004/0092933 A1 | 5/2004 | Shaolian et al. |
| 2004/0149093 A1 | 8/2004 | Tang |
| 2004/0193168 A1 | 9/2004 | Long et al. |
| 2004/0193217 A1 | 9/2004 | Lubbers et al. |
| 2004/0208717 A1 | 10/2004 | Greenhalgh |
| 2004/0220593 A1* | 11/2004 | Greenhalgh ......... A61F 2/2454 606/151 |
| 2004/0260300 A1 | 12/2004 | Gorensek et al. |
| 2004/0267277 A1 | 12/2004 | Zannis et al. |
| 2004/0267317 A1 | 12/2004 | Higgins et al. |
| 2005/0015153 A1 | 1/2005 | Goble et al. |
| 2005/0033362 A1 | 2/2005 | Grafton |
| 2005/0038427 A1 | 2/2005 | Perriello et al. |
| 2005/0049681 A1* | 3/2005 | Greenhalgh ....... A61B 17/0057 623/1.15 |
| 2005/0070906 A1 | 3/2005 | Clark et al. |
| 2005/0080400 A1 | 4/2005 | Corcoran et al. |
| 2005/0137600 A1 | 6/2005 | Jacobs et al. |
| 2005/0137601 A1 | 6/2005 | Assell et al. |
| 2005/0143741 A1 | 6/2005 | Timmermans et al. |
| 2005/0147478 A1 | 7/2005 | Greenberg |
| 2005/0171569 A1* | 8/2005 | Girard ............. A61B 17/00234 606/193 |
| 2005/0177168 A1 | 8/2005 | Brunnett et al. |
| 2005/0187537 A1 | 8/2005 | Loeb et al. |
| 2005/0203527 A1 | 9/2005 | Carrison et al. |
| 2005/0228399 A1 | 10/2005 | Kubo et al. |
| 2005/0251159 A1* | 11/2005 | Ewers ................ A61B 17/0401 606/153 |
| 2005/0251208 A1* | 11/2005 | Elmer ................ A61B 17/0401 606/232 |
| 2005/0261604 A1 | 11/2005 | Stephens et al. |
| 2005/0283156 A1 | 12/2005 | Schmieding et al. |
| 2005/0288710 A1 | 12/2005 | Fallin et al. |
| 2006/0001518 A1 | 1/2006 | Hayashi et al. |
| 2006/0004369 A1 | 1/2006 | Patel et al. |
| 2006/0004410 A1* | 1/2006 | Nobis ................ A61B 17/0401 606/232 |
| 2006/0015108 A1 | 1/2006 | Bonutti |
| 2006/0015110 A1 | 1/2006 | Pepper |
| 2006/0030884 A1* | 2/2006 | Yeung ............... A61B 17/0401 606/232 |
| 2006/0074434 A1 | 4/2006 | Wenstrom et al. |
| 2006/0079904 A1 | 4/2006 | Thal |
| 2006/0100631 A1 | 5/2006 | Sullivan et al. |
| 2006/0155329 A1 | 7/2006 | Grafton et al. |
| 2006/0178748 A1 | 8/2006 | Dinger et al. |
| 2006/0189993 A1 | 8/2006 | Stone |
| 2006/0190042 A1 | 8/2006 | Stone et al. |
| 2006/0212055 A1 | 9/2006 | Karabey et al. |
| 2006/0241675 A1* | 10/2006 | Johnson ................ A61F 2/01 606/200 |
| 2006/0247641 A1 | 11/2006 | Re et al. |
| 2006/0247642 A1 | 11/2006 | Stone et al. |
| 2006/0282085 A1 | 12/2006 | Stone et al. |
| 2006/0293689 A1 | 12/2006 | Miller et al. |
| 2007/0010843 A1 | 1/2007 | Green |
| 2007/0010857 A1 | 1/2007 | Sugimoto et al. |
| 2007/0032800 A1* | 2/2007 | Ortiz ................. A61B 17/0469 606/148 |
| 2007/0093840 A1 | 4/2007 | Pacelli et al. |
| 2007/0167950 A1* | 7/2007 | Tauro ................ A61B 17/0401 606/326 |
| 2007/0185532 A1* | 8/2007 | Stone ................ A61B 17/0401 606/232 |
| 2007/0191853 A1 | 8/2007 | Stone |
| 2007/0213734 A1 | 9/2007 | Bleich et al. |
| 2007/0213735 A1 | 9/2007 | Saadat et al. |
| 2007/0225721 A1 | 9/2007 | Thelen et al. |
| 2007/0233151 A1 | 10/2007 | Chudik |
| 2007/0255317 A1 | 11/2007 | Fanton et al. |
| 2007/0260259 A1 | 11/2007 | Fanton et al. |
| 2007/0276392 A1 | 11/2007 | Beyar et al. |
| 2007/0288023 A1 | 12/2007 | Pellegrino et al. |
| 2007/0288031 A1 | 12/2007 | Dreyfuss et al. |
| 2007/0293879 A1* | 12/2007 | Baker ................ A61B 17/0401 606/151 |
| 2008/0004659 A1 | 1/2008 | Burkhart et al. |
| 2008/0009904 A1 | 1/2008 | Bourque et al. |
| 2008/0027446 A1* | 1/2008 | Stone ................ A61B 17/0401 606/316 |
| 2008/0027457 A1 | 1/2008 | Dienst et al. |
| 2008/0046009 A1 | 2/2008 | Albertorio et al. |
| 2008/0058816 A1 | 3/2008 | Philippon et al. |
| 2008/0065080 A1 | 3/2008 | Assell et al. |
| 2008/0065092 A1 | 3/2008 | Assell et al. |
| 2008/0065114 A1* | 3/2008 | Stone ................ A61B 17/0401 606/139 |
| 2008/0071282 A1 | 3/2008 | Assell et al. |
| 2008/0082127 A1 | 4/2008 | Stone et al. |
| 2008/0082128 A1 | 4/2008 | Stone |
| 2008/0103528 A1* | 5/2008 | Zirps ................ A61B 17/0401 606/232 |
| 2008/0109037 A1 | 5/2008 | Steiner et al. |
| 2008/0114364 A1 | 5/2008 | Goldin et al. |
| 2008/0114399 A1 | 5/2008 | Bonutti |
| 2008/0132932 A1 | 6/2008 | Hoeppner et al. |
| 2008/0140078 A1 | 6/2008 | Nelson et al. |
| 2008/0140092 A1* | 6/2008 | Stone ................ A61B 17/0401 606/144 |
| 2008/0140093 A1 | 6/2008 | Stone et al. |
| 2008/0140116 A1 | 6/2008 | Bonutti |
| 2008/0140123 A1* | 6/2008 | Ferree ................ A61B 17/7022 606/263 |
| 2008/0147063 A1 | 6/2008 | Cauldwell et al. |
| 2008/0147064 A1 | 6/2008 | Cauldwell et al. |
| 2008/0147071 A1 | 6/2008 | Serra et al. |
| 2008/0154275 A1 | 6/2008 | Assell et al. |
| 2008/0161814 A1 | 7/2008 | McAllister et al. |
| 2008/0167660 A1 | 7/2008 | Moreau et al. |
| 2008/0188854 A1 | 8/2008 | Moser |
| 2008/0188935 A1 | 8/2008 | Saylor et al. |
| 2008/0243163 A1 | 10/2008 | Masseglia et al. |
| 2008/0249481 A1 | 10/2008 | Crainich et al. |
| 2008/0255613 A1 | 10/2008 | Kaiser et al. |
| 2008/0262544 A1 | 10/2008 | Burkhart |
| 2008/0275431 A1 | 11/2008 | Stone et al. |
| 2008/0275453 A1 | 11/2008 | Lafosse et al. |
| 2008/0306483 A1 | 12/2008 | Iannarone |
| 2008/0312689 A1* | 12/2008 | Denham ............ A61B 17/0401 606/232 |

(56) References Cited

U.S. PATENT DOCUMENTS

| | | |
|---|---|---|
| 2008/0319478 A1 | 12/2008 | Foerster et al. |
| 2009/0012526 A1 | 1/2009 | Fletcher |
| 2009/0018654 A1 | 1/2009 | Schmieding et al. |
| 2009/0024130 A1 | 1/2009 | Lombardo |
| 2009/0054928 A1 | 2/2009 | Denham et al. |
| 2009/0062854 A1 | 3/2009 | Kaiser et al. |
| 2009/0076514 A1 | 3/2009 | Haines |
| 2009/0082805 A1 | 3/2009 | Kaiser et al. |
| 2009/0099554 A1 | 4/2009 | Forster et al. |
| 2009/0105775 A1 | 4/2009 | Mitchell et al. |
| 2009/0112270 A1 | 4/2009 | Lunn et al. |
| 2009/0112770 A1 | 4/2009 | Schmidt et al. |
| 2009/0131940 A1 | 5/2009 | Brunnett et al. |
| 2009/0138015 A1 | 5/2009 | Conner et al. |
| 2009/0138042 A1 | 5/2009 | Thal |
| 2009/0143784 A1 | 6/2009 | Petersen et al. |
| 2009/0143819 A1* | 6/2009 | D'Agostino ............ A61L 17/12 606/228 |
| 2009/0149858 A1 | 6/2009 | Fanelli et al. |
| 2009/0157081 A1 | 6/2009 | Homan et al. |
| 2009/0157124 A1 | 6/2009 | Ferragamo et al. |
| 2009/0160112 A1 | 6/2009 | Ostrovsky |
| 2009/0171359 A1 | 7/2009 | Sterrett |
| 2009/0192468 A1 | 7/2009 | Stone |
| 2009/0194446 A1 | 8/2009 | Miller et al. |
| 2009/0198258 A1 | 8/2009 | Workman |
| 2009/0210047 A1* | 8/2009 | Amplatz ................ A61F 2/07 623/1.12 |
| 2009/0216238 A1 | 8/2009 | Stark |
| 2009/0216243 A1 | 8/2009 | Re |
| 2009/0221922 A1 | 9/2009 | Lec et al. |
| 2009/0222013 A1 | 9/2009 | Graf et al. |
| 2009/0234386 A1 | 9/2009 | Dean et al. |
| 2009/0234451 A1 | 9/2009 | Manderson |
| 2009/0240104 A1 | 9/2009 | Ogdahl et al. |
| 2009/0240335 A1* | 9/2009 | Arcenio ............ A61B 17/7094 623/17.16 |
| 2009/0248029 A1 | 10/2009 | Paulos |
| 2009/0265002 A1 | 10/2009 | Re et al. |
| 2009/0306671 A1 | 12/2009 | McCormack et al. |
| 2009/0306711 A1* | 12/2009 | Stone ................ A61B 17/0401 606/232 |
| 2009/0312763 A1 | 12/2009 | McCormack et al. |
| 2009/0312776 A1 | 12/2009 | Kaiser et al. |
| 2009/0312792 A1 | 12/2009 | Fallin et al. |
| 2009/0312793 A1 | 12/2009 | Huxel et al. |
| 2009/0318961 A1 | 12/2009 | Stone et al. |
| 2009/0326538 A1 | 12/2009 | Sennett et al. |
| 2010/0023056 A1* | 1/2010 | Johansson .......... A61B 17/0401 606/232 |
| 2010/0049196 A1 | 2/2010 | Re |
| 2010/0049202 A1 | 2/2010 | Re |
| 2010/0049203 A1 | 2/2010 | Re |
| 2010/0057045 A1 | 3/2010 | Albritton, IV et al. |
| 2010/0076440 A1 | 3/2010 | Pamichev et al. |
| 2010/0082033 A1 | 4/2010 | Germain |
| 2010/0087857 A1 | 4/2010 | Stone et al. |
| 2010/0121332 A1 | 5/2010 | Crainich et al. |
| 2010/0121333 A1 | 5/2010 | Crainich et al. |
| 2010/0137679 A1* | 6/2010 | Lashinski ............ A61B 17/0401 600/37 |
| 2010/0145341 A1 | 6/2010 | Ranck et al. |
| 2010/0145384 A1 | 6/2010 | Stone et al. |
| 2010/0152739 A1 | 6/2010 | Sidebotham et al. |
| 2010/0160962 A1 | 6/2010 | Dreyfuss et al. |
| 2010/0185238 A1 | 7/2010 | Cauldwell et al. |
| 2010/0185283 A1 | 7/2010 | Baird et al. |
| 2010/0191241 A1 | 7/2010 | McCormack et al. |
| 2010/0211075 A1 | 8/2010 | Stone |
| 2010/0222881 A1* | 9/2010 | Prewett ................ A61L 31/10 623/11.11 |
| 2010/0234947 A1* | 9/2010 | Ben Rubi .......... A61B 17/0401 623/11.11 |
| 2010/0241121 A1 | 9/2010 | Logan et al. |
| 2010/0249786 A1 | 9/2010 | Schmieding et al. |
| 2010/0262146 A1 | 10/2010 | Tulkis |
| 2010/0262184 A1* | 10/2010 | Dreyfuss ............ A61B 17/0401 606/228 |
| 2010/0268275 A1 | 10/2010 | Stone et al. |
| 2010/0286694 A1 | 11/2010 | Rio et al. |
| 2010/0292713 A1 | 11/2010 | Cohn et al. |
| 2010/0292731 A1 | 11/2010 | Gittings et al. |
| 2010/0292732 A1* | 11/2010 | Hirotsuka .......... A61B 17/0401 606/232 |
| 2010/0292792 A1 | 11/2010 | Stone et al. |
| 2010/0298878 A1 | 11/2010 | Leung et al. |
| 2010/0298879 A1 | 11/2010 | Leung et al. |
| 2010/0305709 A1 | 12/2010 | Metzger et al. |
| 2010/0318122 A1 | 12/2010 | Leung et al. |
| 2011/0009902 A1 | 1/2011 | Leung et al. |
| 2011/0015674 A1 | 1/2011 | Howard et al. |
| 2011/0015675 A1 | 1/2011 | Howard et al. |
| 2011/0022083 A1 | 1/2011 | DiMatteo et al. |
| 2011/0022084 A1 | 1/2011 | Sengun et al. |
| 2011/0046625 A1 | 2/2011 | Boileau et al. |
| 2011/0054526 A1 | 3/2011 | Stone et al. |
| 2011/0087247 A1 | 4/2011 | Fung et al. |
| 2011/0087280 A1 | 4/2011 | Albertorio |
| 2011/0087284 A1 | 4/2011 | Stone et al. |
| 2011/0093010 A1 | 4/2011 | Genova et al. |
| 2011/0098727 A1* | 4/2011 | Kaiser ................ A61B 17/0401 606/144 |
| 2011/0106089 A1 | 5/2011 | Brunnett et al. |
| 2011/0106153 A1 | 5/2011 | Stone et al. |
| 2011/0125189 A1 | 5/2011 | Stoll, Jr. et al. |
| 2011/0152927 A1 | 6/2011 | Deng et al. |
| 2011/0160767 A1 | 6/2011 | Stone et al. |
| 2011/0160768 A1 | 6/2011 | Stone et al. |
| 2011/0184516 A1 | 7/2011 | Baird et al. |
| 2011/0208194 A1 | 8/2011 | Steiner et al. |
| 2011/0208239 A1 | 8/2011 | Stone et al. |
| 2011/0208240 A1 | 8/2011 | Stone et al. |
| 2011/0213416 A1 | 9/2011 | Kaiser |
| 2011/0213417 A1 | 9/2011 | Foerster et al. |
| 2011/0218538 A1 | 9/2011 | Sherman et al. |
| 2011/0218625 A1 | 9/2011 | Berelsman et al. |
| 2011/0224799 A1 | 9/2011 | Stone |
| 2011/0264138 A1 | 10/2011 | Avelar et al. |
| 2011/0264140 A1 | 10/2011 | Lizardi et al. |
| 2011/0264141 A1 | 10/2011 | Denham et al. |
| 2011/0270278 A1 | 11/2011 | Overes et al. |
| 2011/0270293 A1 | 11/2011 | Malla et al. |
| 2011/0270306 A1 | 11/2011 | Denham et al. |
| 2011/0276090 A1 | 11/2011 | Berndt et al. |
| 2011/0295279 A1 | 12/2011 | Stone et al. |
| 2011/0301708 A1 | 12/2011 | Stone et al. |
| 2011/0319896 A1 | 12/2011 | Papenfuss et al. |
| 2012/0004672 A1 | 1/2012 | Giap et al. |
| 2012/0041485 A1 | 2/2012 | Kaiser et al. |
| 2012/0041486 A1 | 2/2012 | Stone et al. |
| 2012/0046693 A1 | 2/2012 | Denham et al. |
| 2012/0053629 A1 | 3/2012 | Reiser et al. |
| 2012/0053630 A1 | 3/2012 | Denham et al. |
| 2012/0053641 A1 | 3/2012 | Meridew |
| 2012/0059417 A1 | 3/2012 | Norton et al. |
| 2012/0059418 A1* | 3/2012 | Denham ................ A61B 17/04 606/232 |
| 2012/0071976 A1 | 3/2012 | May et al. |
| 2012/0089193 A1 | 4/2012 | Stone et al. |
| 2012/0095470 A1 | 4/2012 | Kaiser et al. |
| 2012/0095556 A1 | 4/2012 | Re et al. |
| 2012/0109142 A1 | 5/2012 | Dayan |
| 2012/0109156 A1 | 5/2012 | Overes et al. |
| 2012/0109194 A1 | 5/2012 | Miller et al. |
| 2012/0116452 A1 | 5/2012 | Stone et al. |
| 2012/0123474 A1 | 5/2012 | Zajac et al. |
| 2012/0136388 A1 | 5/2012 | Odermatt et al. |
| 2012/0150203 A1 | 6/2012 | Brady et al. |
| 2012/0150297 A1 | 6/2012 | Denham et al. |
| 2012/0150301 A1 | 6/2012 | Gamache et al. |
| 2012/0160050 A1 | 6/2012 | Nishio et al. |
| 2012/0165866 A1 | 6/2012 | Kaiser et al. |
| 2012/0165867 A1 | 6/2012 | Denham et al. |

(56) References Cited

U.S. PATENT DOCUMENTS

| | | |
|---|---|---|
| 2012/0165938 A1 | 6/2012 | Denham et al. |
| 2012/0172986 A1 | 7/2012 | Stone et al. |
| 2012/0179254 A1 | 7/2012 | Saliman |
| 2012/0180291 A1 | 7/2012 | Oren et al. |
| 2012/0197271 A1* | 8/2012 | Astorino ............ A61B 17/0057 606/148 |
| 2012/0203231 A1 | 8/2012 | Long et al. |
| 2012/0203288 A1 | 8/2012 | Lange et al. |
| 2012/0209325 A1 | 8/2012 | Gagliano et al. |
| 2012/0239085 A1 | 9/2012 | Schlotterback et al. |
| 2012/0239086 A1 | 9/2012 | Reznik et al. |
| 2012/0245585 A1 | 9/2012 | Kaiser et al. |
| 2012/0253355 A1 | 10/2012 | Murray et al. |
| 2012/0265205 A1 | 10/2012 | Steiner et al. |
| 2012/0290002 A1 | 11/2012 | Astorino |
| 2012/0290004 A1 | 11/2012 | Lombardo et al. |
| 2012/0290006 A1 | 11/2012 | Collins et al. |
| 2012/0296345 A1 | 11/2012 | Wack et al. |
| 2012/0296427 A1 | 11/2012 | Conner et al. |
| 2012/0303046 A1 | 11/2012 | Stone et al. |
| 2013/0012962 A1 | 1/2013 | Stone |
| 2013/0018416 A1 | 1/2013 | Lombardo et al. |
| 2013/0023928 A1 | 1/2013 | Dreyfuss |
| 2013/0023929 A1 | 1/2013 | Sullivan et al. |
| 2013/0023930 A1 | 1/2013 | Stone et al. |
| 2013/0035698 A1 | 2/2013 | Stone et al. |
| 2013/0046341 A1 | 2/2013 | Stone et al. |
| 2013/0053897 A1 | 2/2013 | Brown et al. |
| 2013/0072989 A1 | 3/2013 | Overes et al. |
| 2013/0085568 A1 | 4/2013 | Smith et al. |
| 2013/0096611 A1 | 4/2013 | Sullivan |
| 2013/0096612 A1 | 4/2013 | Zajac et al. |
| 2013/0110165 A1 | 5/2013 | Burkhart et al. |
| 2013/0116730 A1 | 5/2013 | Denham et al. |
| 2013/0131722 A1 | 5/2013 | Marchand et al. |
| 2013/0158596 A1 | 6/2013 | Miller et al. |
| 2013/0158601 A1 | 6/2013 | Stone et al. |
| 2013/0165972 A1 | 6/2013 | Sullivan |
| 2013/0190818 A1 | 7/2013 | Norton |
| 2013/0190819 A1 | 7/2013 | Norton |
| 2013/0237997 A1 | 9/2013 | Arai et al. |
| 2013/0238025 A1 | 9/2013 | Howard et al. |
| 2013/0245700 A1 | 9/2013 | Choinski |
| 2013/0268000 A1 | 10/2013 | Harner et al. |
| 2013/0296931 A1 | 11/2013 | Sengun |
| 2013/0317544 A1 | 11/2013 | Ferguson et al. |
| 2013/0325063 A1 | 12/2013 | Norton et al. |
| 2013/0345749 A1 | 12/2013 | Sullivan et al. |
| 2014/0039503 A1 | 2/2014 | Pilgeram |
| 2014/0135835 A1 | 5/2014 | Stone et al. |
| 2014/0163679 A1 | 6/2014 | Re et al. |
| 2014/0188163 A1 | 7/2014 | Sengun |
| 2014/0277121 A1 | 9/2014 | Pilgeram et al. |

FOREIGN PATENT DOCUMENTS

| | | |
|---|---|---|
| DE | 8903079 U1 | 5/1989 |
| DE | 4231101 A1 | 3/1994 |
| DE | 4243715 A1 | 7/1994 |
| DE | 19503504 A1 | 3/1996 |
| EP | 153831 A2 | 9/1985 |
| EP | 253526 A1 | 1/1988 |
| EP | 0440371 A1 | 8/1991 |
| EP | 0611551 A1 | 8/1994 |
| EP | 1155776 A2 | 11/2001 |
| EP | 1174584 A2 | 1/2002 |
| EP | 1369089 A2 | 12/2003 |
| EP | 1398455 A2 | 3/2004 |
| EP | 2277457 A1 | 1/2011 |
| EP | 2286742 A1 | 2/2011 |
| EP | 2544607 A1 | 1/2013 |
| EP | 2548519 A2 | 1/2013 |
| EP | 2596755 A2 | 5/2013 |
| EP | 2662030 A1 | 11/2013 |
| EP | 2662032 A1 | 11/2013 |
| FR | 1166884 A | 11/1958 |
| FR | 2606996 A1 | 5/1988 |
| FR | 2676638 A1 | 11/1992 |
| GB | 2093353 A | 9/1982 |
| WO | 95011631 A1 | 5/1995 |
| WO | 9628100 A1 | 9/1996 |
| WO | 9704908 A1 | 2/1997 |
| WO | 9722301 A1 | 6/1997 |
| WO | 0024327 A2 | 5/2000 |
| WO | 0044291 A1 | 8/2000 |
| WO | 0128457 A1 | 4/2001 |
| WO | 0160268 A1 | 8/2001 |
| WO | 03007861 A1 | 1/2003 |
| WO | 03086221 A1 | 10/2003 |
| WO | 03/092514 A1 | 11/2003 |
| WO | 2004092531 A2 | 10/2004 |
| WO | 2007/010389 A1 | 1/2007 |
| WO | 2008128075 A1 | 10/2008 |
| WO | 2009105880 A1 | 9/2009 |
| WO | 2011112371 A1 | 9/2011 |
| WO | 2012134999 A1 | 10/2012 |
| WO | 2012158583 A1 | 11/2012 |
| WO | 2013006820 A1 | 1/2013 |
| WO | 2014107729 A2 | 7/2014 |

OTHER PUBLICATIONS

Biomet Sports Medicine: Micromax Flex Suture Anchor, (2008).
International Search Report PCT/US2010/042264, dated Sep. 30, 2010.
European Search Report, EP 10173568, dated Nov. 30, 2010.
Chen et al., Journal of Orthopaedic Research, pp. 1432-1438, Nov. 2009.
Chen et al., Poster No. 538, 54th Annual Meeting of the Orthopaedic Research Society, San Francisco, CA Mar. 2008.
HHS Tube, Fort Wayne Metals Research Products Corp., 2009.
Cole et al., American Journal of Sports Medicine, vol. XX, No. X, 2011.
Medtronic, The VISAO High-Speed Otologic Drill Catalog, 2007.
U.S. Appl. No. 13/303,849, filed Nov. 23, 2011.
U.S. Appl. No. 13/368,730, filed Feb. 8, 2012.
Burkinshaw, U.S. Appl. No. 60/418,545, filed Oct. 15, 2002.
U.S. Appl. No. 13/588,586, filed Aug. 17, 2012.
U.S. Appl. No. 13/588,592, filed Aug. 17, 2012.
U.S. Appl. No. 13/783,804, filed Mar. 4, 2013.
U.S. Appl. No. 61/679,336, filed Aug. 3, 2012.
Perthes, German Surgery Periodical, vol. 85, Commermorative Publication, pp. 2-18, 1906.
Perthes, Ober Operationen bel habitueller Schulterluxaton, X, pp. 199-227, 85.
Sugaya et al., Journal of Bone and Joint Surgery, vol. 85-A, No. 5, pp. 878-884, May 2003.
Insall et al., The Journal of Bone and Joint Surgery, vol. 49B, No. 2, pp. 211-228, May 1967.
Chen et al., European Cells and Materials, vol. 16, Supp. 4, p. 7, 2008.
U.S. Appl. No. 13/085,882, filed Apr. 13, 2011.
Extended European Search Report for Application No. EP 12164104 dated Jul. 11, 2012.
International Search Report and Written Opinion for Application No. PCT/US2012/024303 dated May 24, 2012.
Canadian Office Action for Application No. 2773849 dated Aug. 5, 2013.
Canadian Office Action for Application No. 2,812,775 dated Aug. 23, 2013.
U.S. Appl. No. 13/792,982, filed Mar. 11, 2013.
U.S. Appl. No. 13/799,773, filed Mar. 13, 2013.
U.S. Appl. No. 13/182,851, filed Jul. 14, 2011.
U.S. Appl. No. 13/070,692, filed Mar. 24, 2011.
U.S. Appl. No. 12/682,324, filed Sep. 7, 2010.
Stamboulis, et al., "Mechanical properties of biodegradable polymer sutures coated with bioactive glass", Journal of Materials Science: Materials in Medicine, vol. 13, 2002, pp. 843-848.

(56) References Cited

OTHER PUBLICATIONS

Bretca, et al., "Bioactivity of degradable polymer sutures coated with bioactive glass", Journal of Materials Science: Materials in Medicine, vol. 15, 2004, pp. 893-899.
Boccaccini, et al., "Composite Surgical Sutures with Bioactive Glass Coating", J Biomed Mater Res Part B: Appl Biomater 67B, pp. 618-626, 2003.
Canadian Office Action for Application No. 2768020 dated Jan. 21, 2014.
Australian Examination Report for Application No. 2013202699 dated Feb. 21, 2014.
Partial European Search Report for Application No. EP14151822 dated May 16, 2014.
Canadian Office Action for Application No. 2,811,838 dated May 22, 2014.
Extended European Search Report for Application No. EP14159656 dated Jun. 6, 2014.
International Search Report and Written Opinion for Application No. PCT/US2014/021231 dated Jun. 25, 2014.
Extended European Search Report for Application No. EP14157129 dated Oct. 9, 2014.
Partial International Search Report for Application No. PCT/US2014/069087 dated Mar. 12, 2015.
Canadian Office Action for Application No. 2811838 dated Feb. 24, 2015.
International Search Report and Written Opinion for Application No. PCT/US2014/069087 dated Jun. 17, 2015.
Partial European Search Report for Application No. 13162591 dated Aug. 14, 2015.
European Search Report for Application No. 13178933.1 dated Sep. 25, 2015.
Extended European Search Report for Application No. EP14157877 dated Jul. 4, 2016.
Partial European Search Report for Appln No. EP12193507 dated Jun. 30, 2017.

\* cited by examiner

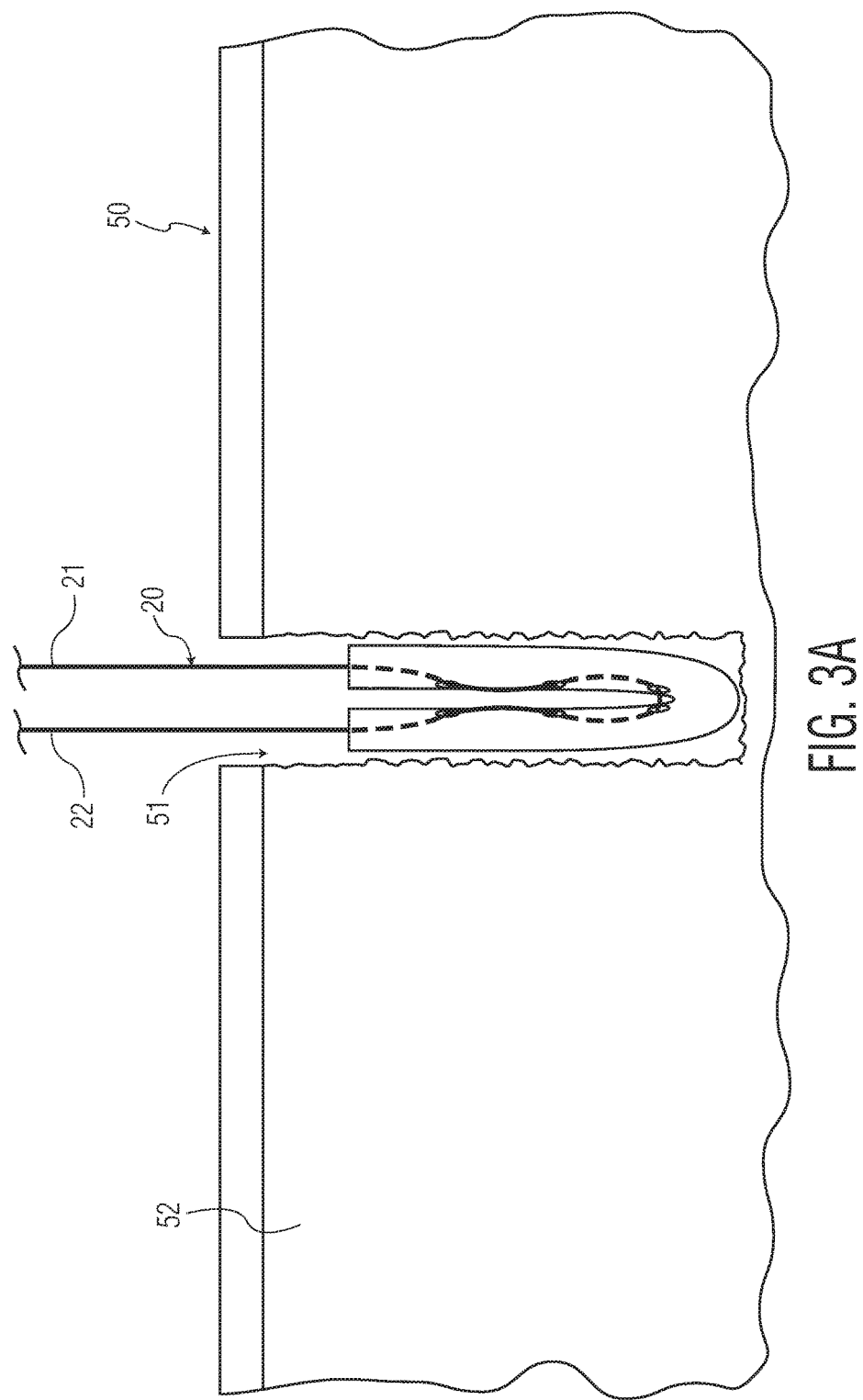

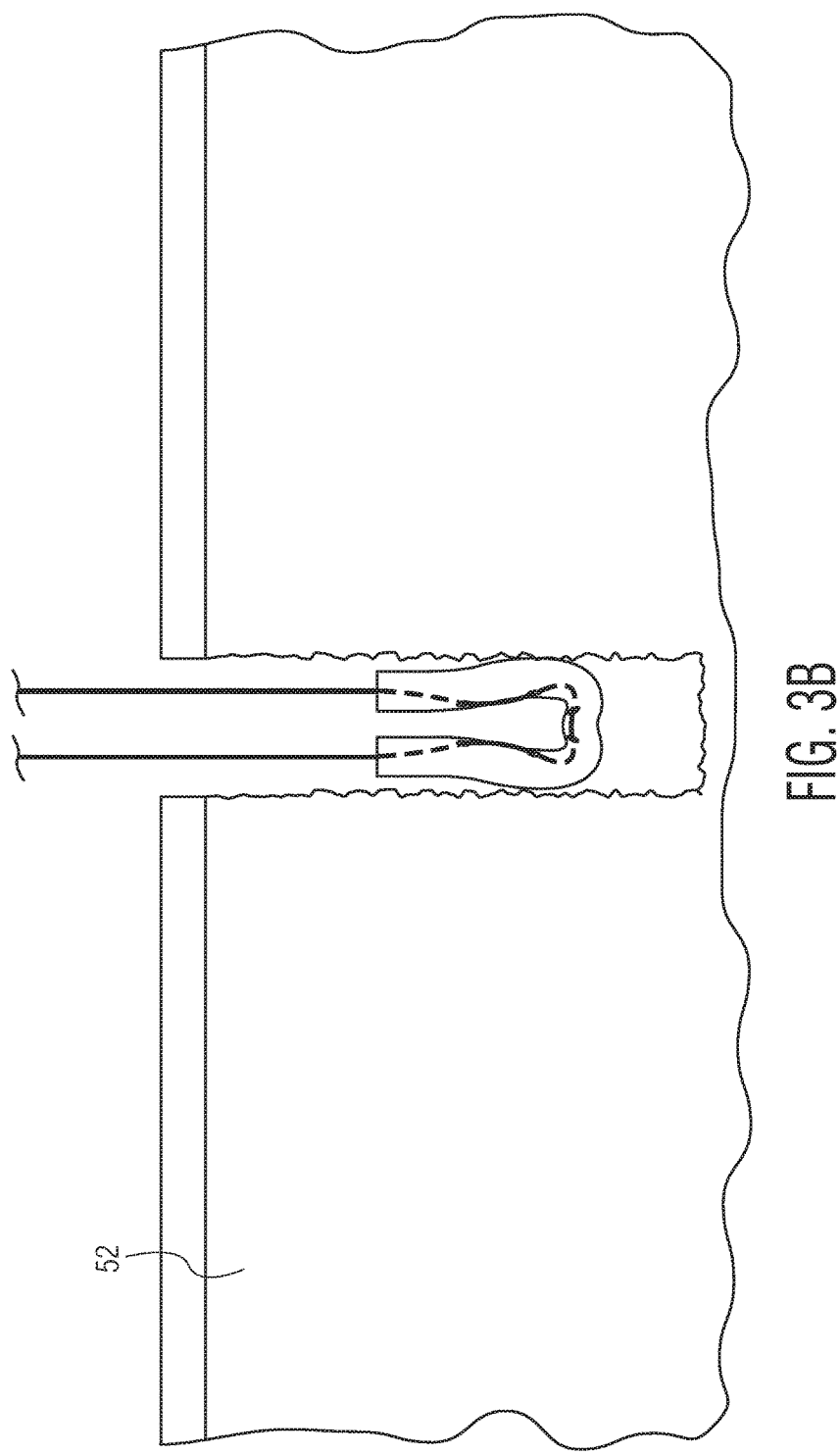

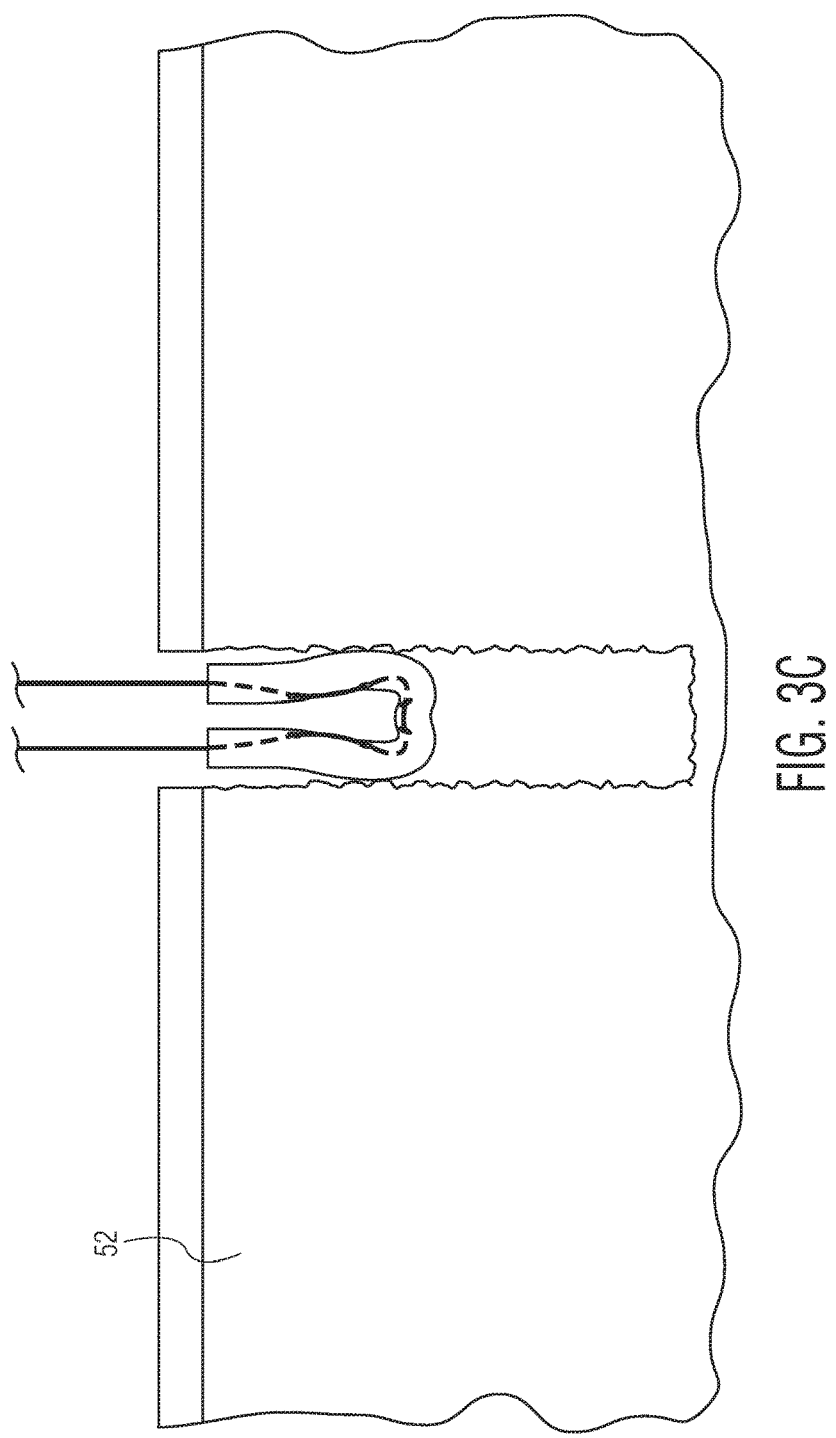

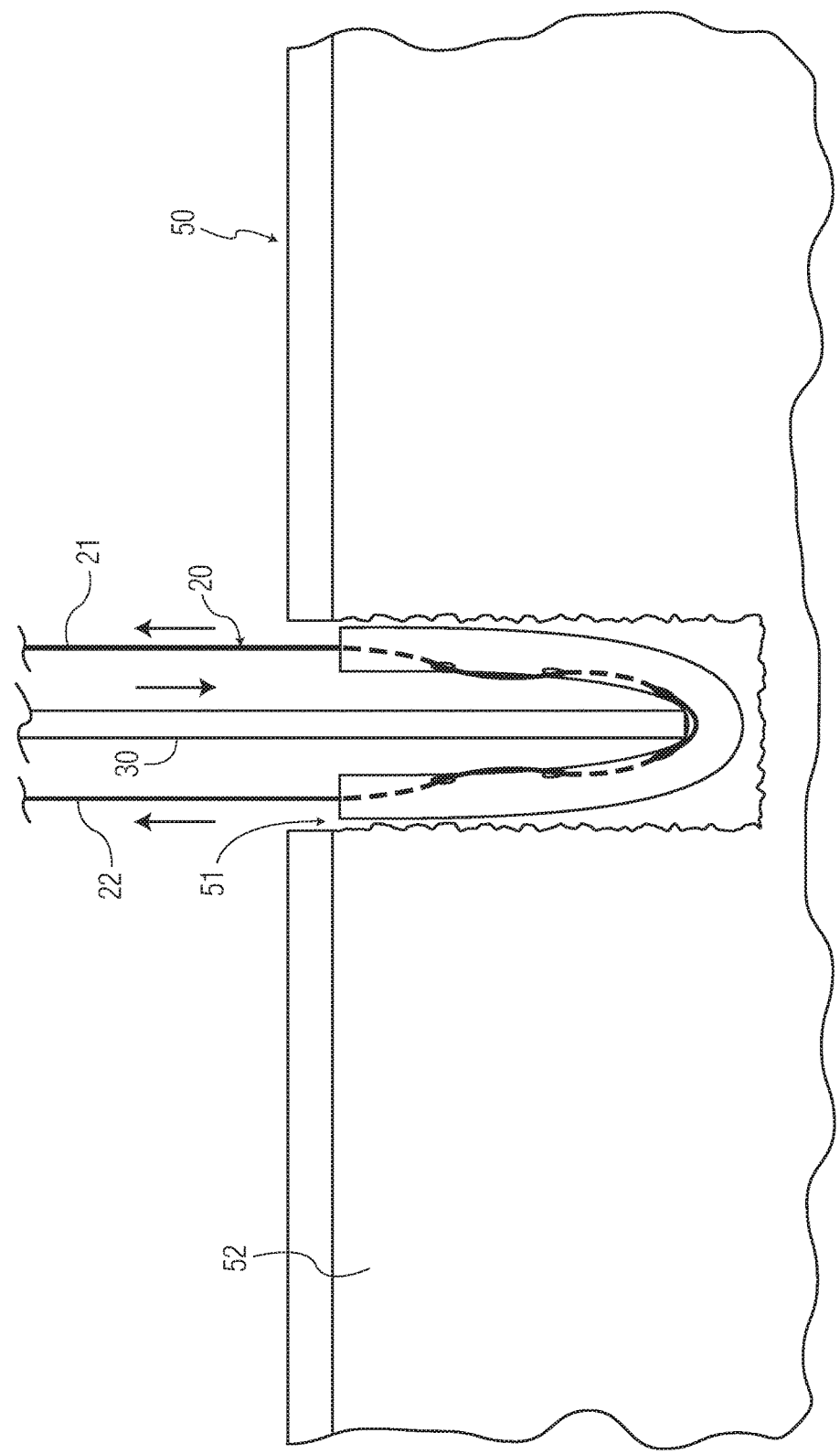

FILAMENTARY FIXATION DEVICE

CROSS REFERENCE TO RELATED APPLICATIONS

This application is a continuation of U.S. application Ser. No. 13/303,849, filed on Nov. 23, 2011, now U.S. Pat. No. 9,445,803, the disclosure of which is incorporated herein by reference.

BACKGROUND OF THE INVENTION

Traditional fixation devices, such as suture anchors or tissue anchors, are typically made of metal or hard plastic, and include a structure which connects or otherwise secures a filament, such as a suture, or a portion of tissue, to the body of the device. In certain applications, these devices have a diameter suitable to hold the devices within a bone. Such devices may also include additional structures to dig into the bone, such as wings, barbs, threads, or the like.

However, such traditional devices tend to be large in diameter, and must include sufficient material, or other additional structures, to withstand the forces pulling against the device, whether via a suture or directly against the device itself. The size of such devices may limit the possible implantation locations in the body, as sufficient bone mass is required to accommodate the device. Moreover, a large hole must be drilled into the bone to allow for passage of the device through the cortical layer and into the cancellous bone. The larger drill holes may be too invasive resulting in excessive loss of healthy bone, or creation of a large repair site, resulting in prolonged recovery time and higher incidence of infection and other complications.

A recent trend in fixation device technology is the "soft" device, also referred to as an "all-suture" fixation device, in which the device itself is constructed of suture-like material. Such all-suture fixation devices may provide solutions to the various problems encountered with traditional devices, as summarized above.

BRIEF SUMMARY OF THE INVENTION

The present invention concerns, generally, a soft fixation device constructed substantially of filamentary material, such as suture or other thread-like material, which is capable of providing high pull-out strength while requiring a small surgical site (e.g., bone hole) as compared to traditional fixation devices. The present invention also includes various embodiments of such soft fixation devices, methods of insertion and related instrumentation, systems and kits. While the majority of embodiments disclosed herein relate to the use of the fixation device of the present invention as a suture anchor for placement in bone, other uses of the fixation device are also possible, many of which are also described herein.

In one embodiment, the present invention includes a fixation device including a sleeve member including an interior and an exterior surface along a length defined between a first end and a second end, and at least two openings positioned along the length and extending from the interior and through the exterior surface; and a filament including a first end and a second end and a length therebetween, the filament positioned relative to the sleeve member such that the filament enters through the first end and into the interior, exits the sleeve member through one of the openings on the exterior surface of the sleeve, re-enters the sleeve member through the other opening on the exterior surface and into the interior, and exits the interior through the second end of the sleeve member. The sleeve member may also be substantially hollow. The filament may further be adapted to be slidable through the interior of the sleeve.

Additionally, the exterior surface of the sleeve member may have at least four openings positioned along its length, such that the filament may enter the interior through the first end, exit the sleeve member through one of the openings on the exterior surface, re-enter the sleeve member through a second opening on the exterior surface and into the interior, exit the sleeve member through a third opening on the exterior surface, re-enter the sleeve member through a fourth opening on the exterior surface and into the interior, and exit the interior through the second end of the sleeve member. Moreover, the exterior surface of the sleeve member may have at least six openings positioned along its length, such that the filament may enter the interior through the first end, exit the sleeve member through one of the openings on the exterior surface, re-enter the sleeve member through a second opening on the exterior surface and into the interior, exit the sleeve member through a third opening on the exterior surface, re-enter the sleeve member through a fourth opening on the exterior surface and into the interior, exit the sleeve member through a fifth opening on the exterior surface, re-enter the sleeve member through a sixth opening on the exterior surface and into the interior, and exit the interior through the second end of the sleeve member.

The sleeve may further be pliable and also expandable or compressible. The filament may also be adapted to be slidable through the sleeve member when the sleeve member is expanded or compressed. The filament may not overlap itself within the interior of the sleeve member. The filament may pass through the interior of the sleeve member in a single direction along the length of the sleeve member.

Moreover, at least one of the filament and the interior may include a coating adapted to improve sliding of the filament through the interior. The exterior surface of the sleeve may also include a coating which may be adapted to allow for tissue ingrowth. The filament may also include a coating adapted to promote healing in adjacent tissue. The filament may also include an at least one indicating marker along its length. Further, the filament may also include multiple colors or patterns along its length, wherein the filament may include one color along a portion of the filament and a second color along another portion of the filament, wherein the colors may provide a distinguishing feature between the two portions of the filament.

In another embodiment, the present invention may include a sleeve member including an interior and an exterior surface along a length defined between a first end and a second end, and at least two openings positioned along the length and extending from the interior and through the exterior surface; and a filament including a first free end and a second free end and a length therebetween, the filament positioned relative to the sleeve member such that the free ends extend from the sleeve member at the first and second ends of the sleeve member, the filament being disposed inside the interior from the first end to a first opening, outside the sleeve member from the first opening to a second opening, and inside the interior from the second opening to the second end of the sleeve member. The sleeve member may further be substantially hollow.

Moreover, the exterior surface of the sleeve member may have at least four openings positioned along its length, such that the filament may be disposed inside the interior from the first end to a first opening, outside the sleeve member from the first opening to a second opening, inside the interior from the second opening to a third opening, outside the sleeve member from the third opening to a fourth opening, and inside the interior from the fourth opening to the second end of the sleeve member. Alternatively, the exterior surface of the sleeve member may have at least six openings positioned along its length, such that the filament may be disposed inside the interior from the first end to a first opening, outside the sleeve member from the first opening to a second opening, inside the interior from the second opening to a third opening, outside the sleeve member from the third opening to a fourth opening, inside the interior from the fourth opening to a fifth opening, outside the sleeve member from the fifth opening to a sixth opening, and inside the interior from the sixth opening to the second end of the sleeve member.

The filament may further be adapted to be slidable through the interior of the sleeve member. At least one of the filament and sleeve member may also include a coating. For example, at least one of the filament and the interior may include a coating adapted to improve sliding of the filament through the interior. In addition to, or alternatively, the exterior surface of the sleeve may include a coating adapted to allow for tissue ingrowth. Further, the filament may include a coating adapted to promote healing in adjacent tissue.

Moreover, the sleeve member may be pliable and maybe expandable or compressible, wherein the filament may be adapted to be slidable through the sleeve member when the sleeve member is expanded or compressed.

Also, the filament may pass through the interior of the sleeve member in a single direction along the length of the sleeve member. The filament may further include an at least one indicating marker along its length. The filament may further include one color along a portion of the filament and a second color along another portion of the filament, wherein the colors provide a distinguishing feature between the two portions of the filament.

In yet another embodiment, the present invention may include a fixation device including a sleeve member including a length, an interior and an exterior surface defined along the length, and at least two openings positioned along the length through the exterior surface; and a filament comprising a first end and a second end and a length therebetween, the filament positioned relative to the sleeve member such that the filament exits the sleeve member through one of the openings on the exterior surface of the sleeve and re-enters the sleeve member through the other opening on the exterior surface and into the interior such that the filament passes through the interior of the sleeve member in a single direction and is adapted to be slidable through the interior of the sleeve member along the length of the filament. The sleeve member may also be substantially hollow and may further include a first end and a second end at respective ends of the length, and the filament may thus enter the interior of the sleeve member through the first end and exit through the second end.

Additionally, the exterior surface of the sleeve member may have at least four openings positioned along its length, such that the filament may enter the interior through the first end, exit the sleeve member through one of the openings on the exterior surface, re-enter the sleeve member through a second opening on the exterior surface and into the interior, exit the sleeve member through a third opening on the exterior surface, re-enter the sleeve member through a fourth opening on the exterior surface and into the interior, and exit the interior through the second end of the sleeve member. Moreover, the exterior surface of the sleeve member may have at least six openings positioned along its length, such that the filament may enter the interior through the first end, exit the sleeve member through one of the openings on the exterior surface, re-enter the sleeve member through a second opening on the exterior surface and into the interior, exit the sleeve member through a third opening on the exterior surface, re-enter the sleeve member through a fourth opening on the exterior surface and into the interior, exit the sleeve member through a fifth opening on the exterior surface, re-enter the sleeve member through a sixth opening on the exterior surface and into the interior, and exit the interior through the second end of the sleeve member.

In a further embodiment, the present invention may include a fixation device including a sleeve member including an interior and an exterior surface along a length defined between a first end and a second end, and at least two openings positioned along the length and extending from the interior and through the exterior surface; and a filament including a first end and a second end, a length therebetween, and an at least one indicating marker positioned along its length, the filament positioned relative to the sleeve member such that the filament enters through the first end and into the interior, exits the sleeve member through one of the openings on the exterior surface of the sleeve, re-enters the sleeve member through the other opening on the exterior surface and into the interior, and exits the interior through the second end of the sleeve member. The sleeve member may also be substantially hollow. The filament may further be adapted to be slidable through the interior of the sleeve. The indicating marker may be adapted to provide guidance to an operator that proper deployment of the device has occurred.

In yet a further embodiment, the present invention may include a fixation device including a sleeve member including an interior and an exterior surface along a length defined between a first end and a second end, and at least two openings positioned along the length and extending from the interior and through the exterior surface; and a filament including a first end and a second end and a length therebetween, the filament positioned relative to the sleeve member such that the filament enters through the first end into the interior, sequentially exits and re-enters the sleeve member through consecutive openings on the exterior surface of the sleeve, and exits the interior through the second end of the sleeve member such that the filament is disposed outside of the sleeve member in X regions along the length of the sleeve member, is disposed inside the interior in X+1 regions along the length or the sleeve member, and passes through openings numbering 2X, wherein X≥1. The sleeve member may also be substantially hollow. The filament may further be adapted to be slidable through the interior of the sleeve.

In another embodiment, the present invention may include a system including a fixation device including a sleeve member including an interior and an exterior surface along a length defined between a first end and a second end, and at least two openings positioned along the length and extending from the interior and through the exterior surface; and a filament including a first end and a second end, and a length therebetween, the filament positioned relative to the sleeve member such that the filament enters through the first end and into the interior, exits the sleeve member through one of the openings on the exterior surface of the sleeve, re-enters the sleeve member through the other opening on the exterior surface and into the interior, and exits the interior through the second end of the sleeve member; and an inserter. The inserter may include a distal tip which engages a portion of the fixation device. Further, the distal tip may engage, directly, both a portion of the sleeve and a portion of the filament which has exited the sleeve member through one of the openings.

In yet another embodiment, the present invention may include a method for securing a filament in a hole in a bone, including: accessing the bone and preparing a bone hole; inserting a fixation device into the bone hole, the device including a sleeve member including an interior and an exterior surface along a length defined between a first end and a second end, and at least two openings positioned along the length through the exterior surface; and a filament including a first end and a second end and a length therebetween, the filament positioned relative to the sleeve member such that the filament enters through the first end and into the interior, exits the sleeve member through one of the openings on the exterior surface of the sleeve, re-enters the sleeve member through the other opening on the exterior surface and into the interior, and exits the interior through the second end of the sleeve member; and compressing the sleeve member within the bone hole. As to the compressing step, the two ends of the filament may be pulled. Alternatively, the compressing step may include sequentially pulling on one end of the filament and pulling on the other end of the filament. This method may further include the step of adjusting the filament by pulling on at least one of the two ends of the filament to slide the filament through the sleeve member. Further, the step of compressing the sleeve member may change the shape of the sleeve member from a substantially U-shape to a substantially W-shape. In a further step, this method may include using the filament secured in bone to thereby secure tissue to the bone, including the steps of passing at least one end of the filament through the tissue and securing the tissue to the bone by securing the filament thereto. The filament may be secured to the tissue, to thereby secure the tissue to bone, through a knot or the like.

In a further embodiment, the present invention may include a method for securing a tissue to a bone, including: accessing the bone and preparing a bone hole; inserting a fixation device into the bone hole, the device including a sleeve member having an interior and an exterior surface along a length defined between a first end and a second end, and at least two openings positioned along the length through the exterior surface; and a filament including a first end and a second end and a length therebetween, the filament positioned relative to the sleeve member such that the filament enters through the first end and into the interior, exits the sleeve member through one of the openings on the exterior surface of the sleeve, re-enters the sleeve member through the other opening on the exterior surface and into the interior, and exits the interior through the second end of the sleeve member; pulling on the two ends of the filament to compress the sleeve member within the bone hole; adjusting the filament by pulling on at least one of the two ends of the filament; passing at least one end of the filament through the tissue; and securing the tissue to the bone by securing the filament thereto. The tissue may be a portion of a rotator cuff, a portion of a shoulder labrum, a portion of a hip labrum, or another soft tissue, any of which may be reattached to the bone at a reattachment site at or adjacent to the bone hole. This device can also be deployed into soft tissue to secure soft tissue to soft tissue such as meniscal repair or the like. Furthermore, this device can also be deployed into bone to secure bone to bone such as fracture fixation or the like.

BRIEF DESCRIPTION OF THE DRAWINGS

FIG. 3A illustrates one embodiment of a method of insertion of the fixation device of FIG. 1, wherein the fixation device is positioned within a hole prepared in a bone; FIG. 3B illustrates the fixation device of FIGS. 1 and 2, in which the filament 20 is tensioned and the fixation device is compressed; and FIG. 3C illustrates potential migration of the fixation device proximally, towards the cortical bone.

FIG. 4 illustrates one embodiment of a method of insertion of the fixation device of FIGS. 1 and 2, in which an insertion tool is used to implant the fixation device within a hole prepared in a bone.

DETAILED DESCRIPTION

The fixation device, and associated systems, kits and methods, of the present invention are intended for use in tissue, such as bone or soft tissue. Soft tissue may be, for example, meniscus, cartilage, ligaments and tendons, or the like. While many of the exemplary methods disclosed herein are directed towards its use as a suture anchor for implantation into a bone hole, other uses, some of which are described herein, are also envisioned. As used herein, "proximal" or "proximally" means closer to or towards an operator, e.g., surgeon, while "distal" or "distally" means further from or away from the operator.

Figure 1:
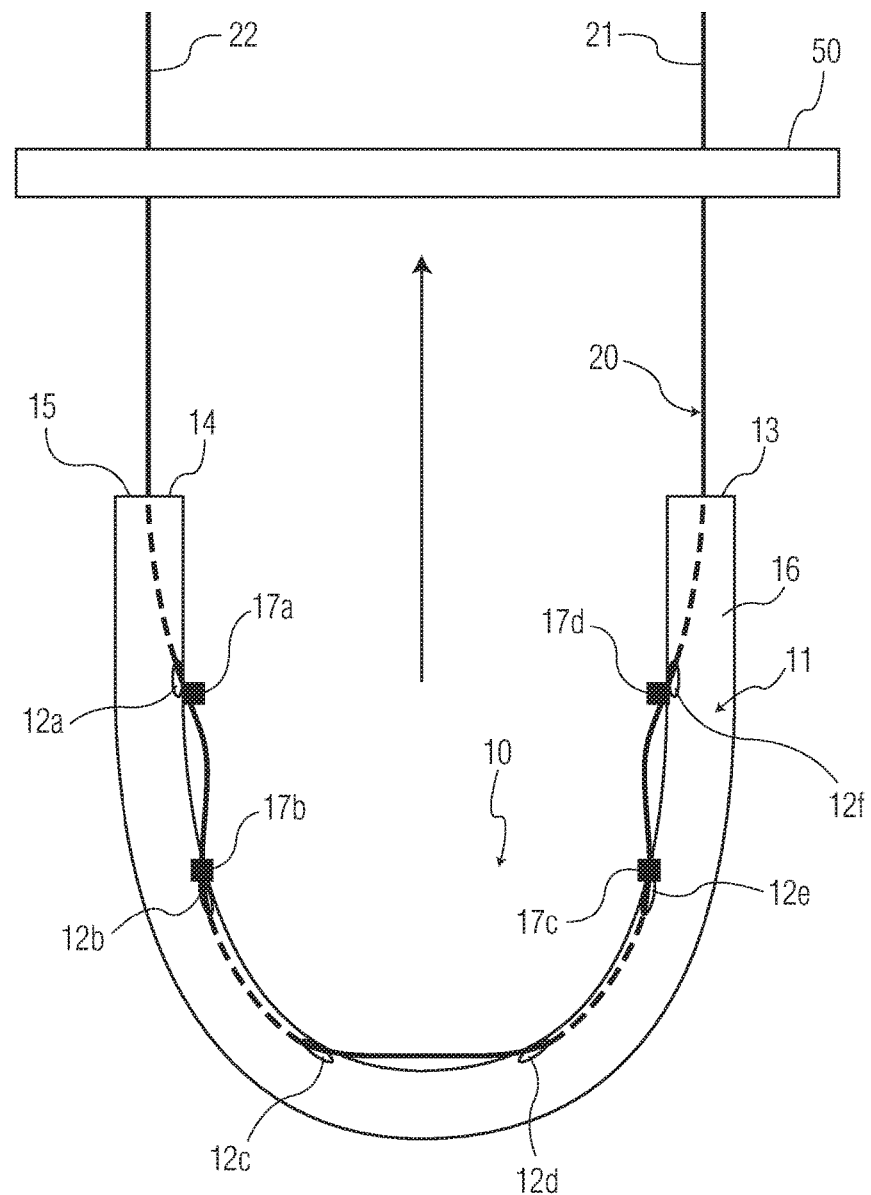
FIG. 1 illustrates one embodiment of a fixation device of the present invention.
Figure 2:
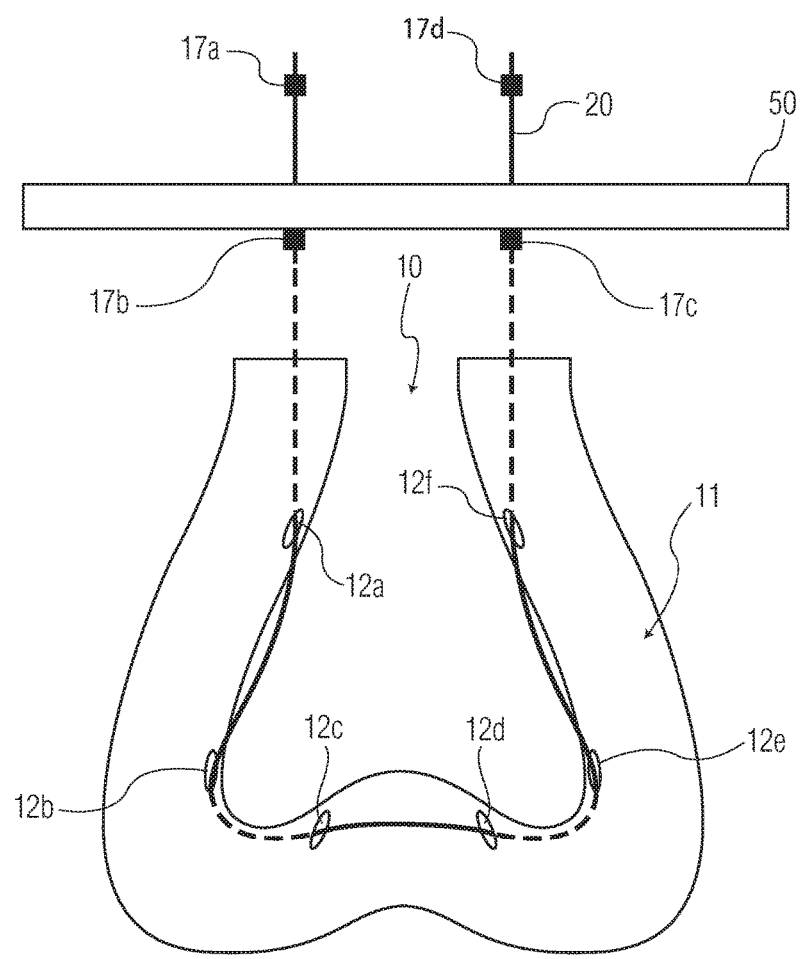
FIG. 2 illustrates the fixation device of FIG. 1 after tensioning of the filament 20.

In a first embodiment, illustrated in FIGS. 1 and 2, the fixation device 10 of the present invention includes a sleeve member 11 and a filament 20. The sleeve member 11 includes an interior 15 and an exterior surface 16, both of which extend along a length defined between a first end 14 and a second end 13. The sleeve member 11 may be substantially hollow. The exterior surface also includes at least two openings 12c, 12d positioned along the length of the exterior surface 16, each of which form a passageway through the exterior surface and into the interior 15. As illustrated, though, the exterior surface may include more than two openings, and may include four openings (for example, 12a, 12b, 12e, 12f), six openings (for example, 12a, 12b, 12c, 12d, 12e, 12f), or any other number of openings in any configuration positioned along the length of the exterior surface. The various openings 12 may be prepared, for example, during the weaving process forming the sleeve 11 or, alternatively, the openings may be formed after the sleeve has been woven, such as by the use of a needle, knife, or other tool capable of forming the openings.

The filament 20 includes a length and at least a portion of the length of the filament is positioned within the interior 15 of sleeve 11. The filament also includes first and second free ends 21, 22. The filament is slidable within the interior 15. The filament may also pass through at least one of the openings 12 along the exterior surface 16 of the sleeve 11. For example, as in FIG. 1, filament 20 may exit the interior 15 through opening 12c and re-enter the interior through opening 12d.

In one embodiment, the fixation device 10 of the present invention may include a sleeve member 11 including an interior 15 and an exterior surface 16 along a length defined between a first end 14 and a second end 13, and at least two openings 12 positioned along the length and extending from the interior and through the exterior surface; and a filament 20 including a first free end 22 and a second free end 21 and a length therebetween, the filament positioned relative to the sleeve member such that the free ends extend from the sleeve member at the first and second ends of the sleeve member, the filament being disposed inside the interior from the first end 14 to a first opening 12a, outside the sleeve member from the first opening to a second opening 12b, and inside the interior from the second opening to the second end 13 of the sleeve member. The sleeve member may further be substantially hollow.

Figure 14A:
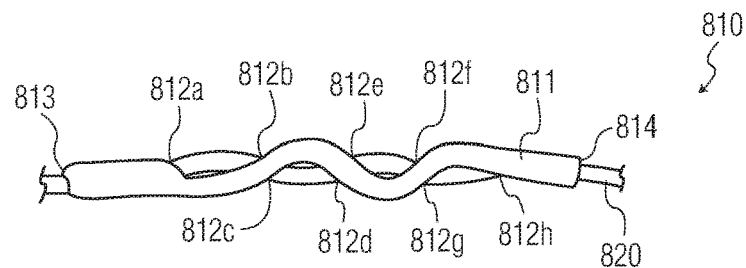
FIGS. 14A-C illustrate a further embodiment of a fixation device of the present invention.
Figure 14B:
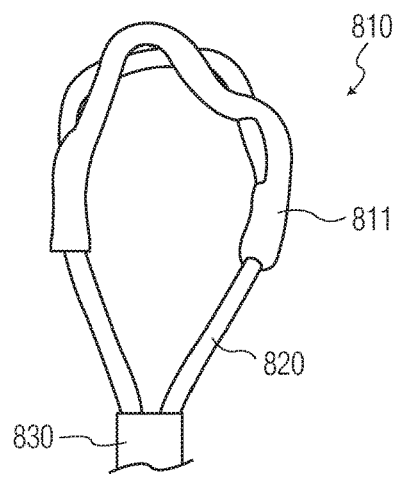
Figure 14C:
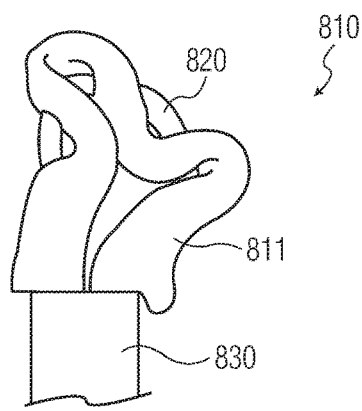
Figure 15A:
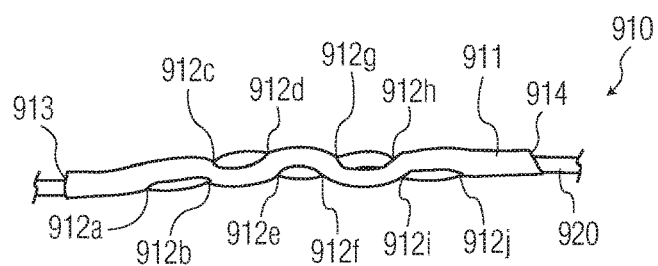
FIGS. 15A-C illustrate still another embodiment of a fixation device of the present invention.
Figure 15B:
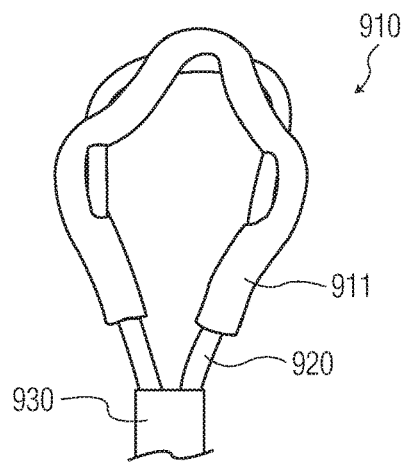
Figure 15C:
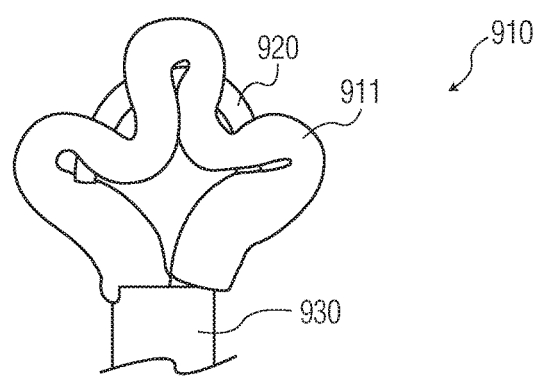
Figure 16A:
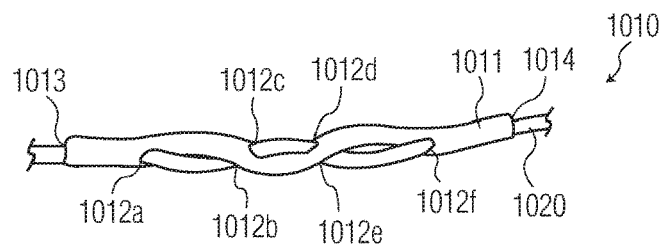
FIGS. 16A-C illustrate another embodiment of a fixation device of the present invention.
Figure 16B:
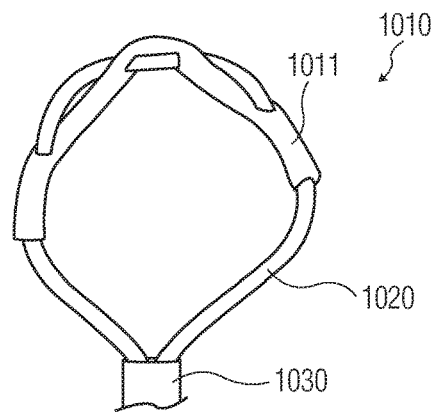
Figure 16C:
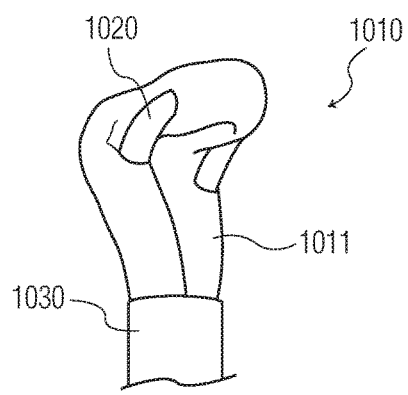

Put another way, in one embodiment, the present invention may include a fixation device including a sleeve member including an interior and an exterior surface along a length defined between a first end and a second end, and at least two openings positioned along the length and extending from the interior and through the exterior surface; and a filament including a first end and a second end and a length therebetween, the filament positioned relative to the sleeve member such that the filament enters through the first end into the interior, sequentially exits and re-enters the sleeve member through consecutive openings on the exterior surface of the sleeve, and exits the interior through the second end of the sleeve member such that the filament is disposed outside of the sleeve member in X regions along the length of the sleeve member, is disposed inside the interior in X+1 regions along the length or the sleeve member, and passes through openings numbering 2X, wherein X≥1. The various exemplary embodiments illustrated in this application show that, for example, X=2 (as in FIGS. 5-6, for example); X=3 (as in FIGS. 1-4, 7-13 and 16, for example); X=4 (as in FIGS. 14A-C, for example); X=5 (as in FIGS. 15A-C).

The filament 20 may be, for example, a length of suture or other such material. The filament may be substantially hollow or substantially solid, and may further have a substantially round or substantially flat (e.g., tape) shape. The filament may also include, for example, a relatively stiff portion, relative to the rest of the filament, which can provide beneficial uses such as for simpler threading through small devices, such as a fixation device like a ReelX suture anchor (Stryker Endoscopy, San Jose, Calif.), or to provide a stiff portion which may be pushed through a cannula or other instrument, such as a suture passer. The sleeve 11 may also be, for example, a suture or other such material that is substantially hollow forming the interior 15. The sleeve, like the filament, may also include a stiff portion or portions which may provide for better placement on an inserter, such as by helping the sleeve to fold around the end of the inserter. Both the sleeve and the filament may be constructed by known means, such as by braiding multiple filaments together, as is the normal manufacturing process of sutures and the like. Either or both of the filament and sleeve may be constructed of synthetic material (e.g., PLGA, UHM-WPE, or the like) or of organic material (silk, animal tendon, or the like).

The filament 20 may also optionally include at least one indicating marker 17a, 17b, 17c and 17d which may indicate to an operator, such as a surgeon, whether or not the device 10 is properly positioned and/or compressed, as will be explained in greater detail below. The indicating marker may be, for example, a spot (as illustrated), a radial ring, a portion having a differing color from the rest of the filament, or the like. In another example, the indicating markers 17a-d of the filament 20 may be a portion of the filament 20 being of a different color than the rest of the filament. In this example, the portion of filament 20 between reference numbers 17a and 17b, and between 17c and 17d, may be of a different color than the remainder of the filament 20. Such contrasting colors of these portions may provide a clear indication to the operator when performing a surgical procedure, and may be of particular use in arthroscopic procedures.

Further, the filament 20 may also include a color or other pattern along its length. For example, the filament 20 may be of a certain color such that an operator may know which suture, among numerous others which may be present at the surgical site, is the filament 20. Moreover, filament 20 may have multiple colors or patterns along its length, other than those represented as the at least one indicating marker. For example, one half of the filament 20 may be one color, and the other half of the filament may be a different color. If the particular surgery requires that the two ends of filament 20 be tied together, such as by a slip knot, the two different colors may assist the operator in knowing which half of the filament should be used as the post and which half should be used to tie the slip knot around the post. Such a decision would be based on the particular surgical procedure being performed. Of course, the two differing colors may cover different amount of the length of the filament, however, the differing colors may be most useful if they cover at least the two free ends or end portions 21, 22 of the filament such that an operator can easily differentiate between the two lengths of the filament.

The sleeve has a diameter at least as large as the filament such that the sleeve has an inner diameter of sufficient size to allow the filament to pass therethrough and be slidable therein. Various arrangements of sizes of filament and sleeve are envisioned, so long as the filament remains slidable through the sleeve. For example, in one embodiment, the filament 20 may be a #2 suture while the device 10, positioned on an inserter, may have a diameter of about 1.2 mm. In one exemplary use of the device, where the device is positioned within a bore hole in tissue, such as bone, this sized device 10 may be positioned within a bore hole in tissue having a diameter of about 0.8-1.6 mm, preferably about 1.20-1.45 mm. In an alternative embodiment of the device 10, two filaments 20 may be included within a single sleeve 11, where the filaments are both #2 suture and the device 10, positioned on an inserter, may have a diameter of about 1.8-2.6 mm, and preferably about 1.9 mm. This sized device may also be positioned, for example, within a bore hole in tissue having a diameter of about 1.5-3.0 mm, preferably about 1.9-2.3 mm. This size of a bore hole may also be used for an alternative embodiment of the device 10 including three filaments 20 within a single sleeve 11. During use, the sleeve, being a length of filamentary material, may stretch or otherwise expand such that the effective diameter of the sleeve may be larger than the examples provided above. Of course, many other configurations of filament and sleeve sizes are envisioned depending on the surgical location and procedure.

Additionally, the sleeve is flexible and is further expandable and compressible which may allow the sleeve, upon tensioning of the filament to, for example, adjust from a substantially U-shape (e.g, FIGS. 1, 3A) and compact or crush, or otherwise compress, to a substantially W-shape (e.g., FIGS. 2, 3B-C). As the sleeve compresses, the diameter of the sleeve may increase and the height of the sleeve may decrease. This shape change during compression provides for increased pullout strength as the sleeve further engages the cancellous bone and/or cortical bone in this compressed shape, as seen for example in FIGS. 3B-C.

The pullout strength may also depend on the positioning of the openings 12 along the sleeve, and particularly, the positioning of the middle openings, which are positioned toward the base of the U-shape, prior to compression of the sleeve, and which, during compression, assist in forming the W-shape of the sleeve. For example, as to the embodiment of FIGS. 1-4, the openings 12*c* and 12*d* may be spaced apart at a distance such that at least 3 mm of filament spans the distance between the openings 12*c*, 12*d*, and more preferably, at least 6 mm of filament span the distance between the openings 12*c*, 12*d*. Such distance between openings 12*c*, 12*d* may allow for a larger amount of sleeve material to be present between the openings, such that as the sleeve is compressed, this larger amount of material creates a W-shape, as in FIG. 3B-C, which may affect an increased pullout strength of the device. If less than 3 mm of filament spans between openings 12*c*, 12*d*, there will also be less sleeve material between the openings, which may result in decreased pullout strength due to less material forming the middle of the compressed W-shape. Moreover, as discussed in greater detail below, the span of filament, outside of the sleeve, between openings 12*c* and 12*d* may allow for better seating on an insertion device 30 (FIG. 4) such that, for example, the device 10 may fit through a smaller bore hole in a tissue than if the filament were positioned within the sleeve between openings 12*c* and 12*d*.

Similarly, the openings near the ends of the sleeve, for example, openings 12*a*, 12*f* of FIG. 1, may be positioned at least 3 mm from the ends 13, 14 of the sleeve to maintain sleeve strength. If the openings 12*a*, 12*f* are placed too close to the ends, such as less than 3 mm away from the ends, the sleeve may break during compression, which may result in decreased pullout strength.

The fixation device is constructed, in one embodiment, by weaving two separate filament-like structures, the sleeve 11 and the filament 20, using known materials (such as sutures or the like) in a specific weaving process. In one example, a needle (not shown) may be used to pass the filament 20 (attached to the needle) through the interior 15 of the sleeve, from the first end 14 to the second end 13. The filament may be directed through the various openings 12 through the sleeve 11 and finally be pulled out through the second end 14. Following assembly, the fixation device 10 is now ready for packaging, sterilization, and subsequent use. In order to allow for proper sliding of the filament 20 through the sleeve 11, the filament may be passed through the interior of the sleeve such that the filament does not overlap itself, as can be seen in the various embodiments illustrated in the figures. As can also be seen in the various figures, in order to allow for the sliding of the filament 20, the filament is passed through the interior of the sleeve member in a single direction along the length of the sleeve member. Such configurations of the sleeve and filament may provide decreased friction between the sleeve and filament such that the filament has an increased ability to slide, even when the sleeve is compressed.

Sliding of the filament 20 within the sleeve 11 may be improved through the introduction of a coating on at least one of the interior 15 of the sleeve and the filament 20. Suitable coatings may include PTFE or the like which minimizes friction between the filament and the sleeve and improves sliding.

Other coatings may also be applied to at least one of the filament and sleeve. For example, the exterior surface 16 of the sleeve 11 may have a coating suitable for allowing tissue ingrowth. Such a suitable coating may be hydroxyapatite powder or tricalcium phosphate for promoting bone ingrowth. Other coatings may include collagen-based additives, platelet-rich plasma, bioactive glass, or the like, to be used depending on the type of tissue into which the device 10 is being placed.

The device 10 may be positioned on an inserter 30 which may assist an operator in positioning the device within a bone hole. The inserter 30 may include a distal end 31 on which the device 10 is positioned. The distal end 31 may be a blunt end, as illustrated in FIG. 4. Alternatively, the inserter distal end may be a forked end, such that the sleeve 11 nests within the fork, or may have an active clamping structure, similar to a forceps or the like, which can optionally engage or disengage the sleeve 11 as needed. Of course, the distal end 31 must have a sufficiently small size to maintain the usefulness of the small diameters of the fixation device, and the intended benefit of the device being implanted into a smaller diameter bone hole, particularly when the fixation device is to be implanted using an arthroscopic technique.

Furthermore, as illustrated in FIG. 4, this embodiment of fixation device may provide for better loading onto an inserter due to at least the relationship between the sleeve and the filament between openings 12*c* and 12*d*. Specifically, because the filament is outside the sleeve between these openings, the device may be more easily loaded onto the inserter because the sleeve and filament can be stacked atop one another. Additionally, for example, such a setup may allow the operator to prepare an even smaller tissue hole for implantation of the device 10 since the device, between openings 12*c* and 12*d*, has an even smaller diameter than, for example, other embodiments, such as for example the embodiment of FIGS. 5 and 6, where the filament 120 is inside the sleeve between openings 112*b* and 112*c*, such that the sleeve and filament are instead, effectively, a single larger structure.

As mentioned above, other embodiments of the fixation device may include a single sleeve having two or more filaments positioned within its interior. In one example of a sleeve having two filaments positioned therethrough, a first filament may, similar to filament 20 of FIG. 1, pass through the various openings of the sleeve. The second filament, however, may either also pass through the openings of the sleeve, or stay within the interior of the sleeve along the entire length of the sleeve. In a further example, where three sutures are positioned within a single sleeve, the first filament may pass through the sleeve, and openings, therein, as illustrated in FIG. 1. The second filament may either stay entirely within the interior of the sleeve along the length of the sleeve or may also pass through the openings of the sleeve, as in FIG. 1. The third filament may also either stay entirely within the interior of the sleeve along the length of the sleeve or may also pass through the openings of the sleeve, as in FIG. 1. Of course, further alternative arrangements are envisioned, including, for example, arrangements where one of the filaments only passes through a couple of the openings present in the sleeve.

In use, one embodiment of which is illustrated in FIGS. 1-3, the sleeve 11 may be used in a method of anchoring a filament 20 in a bone. Using a drill and drill guide (not shown), such as that found in U.S. application Ser. No. 12/821,504, filed Jun. 23, 2010, the entirety of which is incorporated by reference herein as if fully set forth herein, or other drill and drill guide known in the art, a drill hole 51 is prepared in bone 50 where it is desired to anchor a filament 20. The drill and drill guide may include a laser etching, or similar marking, or alternatively a hard stop between the drill and drill guide, to ensure proper drilling depth. For example, the hole may be prepared in the shoulder joint to repair labral tissue which has separated from the glenoid. The diameter of the hole may be, for example, about equal to the diameter of the sleeve itself, such that, the device, folded on itself, will compress and fit snuggly within the bone hole, even prior to deployment of the device, as will be discussed below. Thus, for example, for a 1.2 mm sleeve, the drill hole may have a diameter of about 1.2 mm, and for a 1.8 mm sleeve, the diameter of the drill hole may be about 1.8 mm. Such matching of drill hole to device diameter may create a press-fit connection between the device the bone hole, providing initial contact between the device and the bone, prior to deployment of the device. The depth of the drill hole is dependent on the particular anatomy in which the device is to be implanted, but the depth may be, for example, typically between about 13-25 mm. In any event, the drill hole should pass through the cortical bone and enter into the cancellous bone 52. It should be noted that, if a straight guide, as is known in the art, is used, then these measurements should be used, depending on the size of the sleeve. However, if a curved guide is used, such as the above guide incorporated by reference, then the operator may, optionally, wish to make the bore hole slightly larger to ensure placement of the sleeve completely into the bore hole upon exiting the curved guide. As discussed below, upon deployment of the device, sufficient contact between the bone hole and the device may still be achieved to attain required pullout strength.

Once the hole is prepared, the drill is removed from the drill guide, and the drill guide may remain firmly in place at the bone hole. The device 10, positioned on an insertion tool 30, may then be passed through the drill guide (not shown) and to the hole in the bone, as illustrated in FIG. 4, for example. The sleeve 11 is then pressed into the bone hole, with the filament 20 positioned through the interior as illustrated, and may optionally be placed in the bone hole by lightly malleting using a mallet or like instrument to firmly seat the sleeve in the bone hole. Optionally, the inserter may have a laser etching, or other marking, which may assist the operator in accomplishing a proper insertion depth into the bone hole. At this point in the procedure, as illustrated in FIGS. 3A and 4, the device 10 is substantially folded in half within the bone hole, such that the two halves contact the bone hole side walls along a portion of their length. Such initial contact may achieve a press-fit engagement between the bone hole and the device such that the device is frictionally engaged by the bone hole which may provide initial friction to maintain the device within the bone hole, particularly, as below, when the inserter 30 is being removed from the bone hole. As in FIG. 3A, the fixation device may be placed as deeply as possible into the bone hole such that a portion of it may contact the floor of the bone hole. While not necessary, such placement may allow for maximum room for any potential upward migration of the fixation device within the bone hole.

Once the bone hole has been prepared, and the fixation device is positioned within the bone hole, the fixation device may then be deployed. As illustrated in FIGS. 3A and 3B, the inserter tool has been removed from the drill guide by pulling the inserter directly back through and out of the guide. The operator may then grasp the ends 21, 22 of the filament 20 which are extending from sleeve 11. Optionally, these filament ends may be removably secured to the handle (not shown) of the inserter for ease of locating and for organizational benefits. The operator then may tension the ends of the filament 20, which may be accomplished with a single, continuous pull on the filament ends, to compress and set the sleeve 11 within the hole in the bone such that the sleeve compresses from its U-shape of FIG. 1 towards the W-shape of FIG. 2. Such compression occurs from the bottom of the U-shape upwards, as in FIGS. 3A-B, such that the bottom of the U-shape compresses towards the ends 13, 14 (although some downward compression of the ends 13, 14 towards the bottom of the U-shaped sleeve may also occur). Such compression may, as illustrated for example in FIG. 3A, lift the sleeve 11 from the floor of the bone hole. Further tensioning on the filament ends 21, 22 may result, as illustrated in FIG. 3C, in migration of the fixation device 10 proximally within the bone hole and towards the cortical bone 50. Such proximal migration of the fixation device may result in even further compression of the sleeve 11 as well as additional frictional engagement with the bone hole walls. In a further example, the sleeve 11 may migrate proximally until it contacts the underside of the cortical bone layer 50, such that the sleeve 11 may be prevented from further movement, e.g., out of the bone hole, by its engagement against the underside of the cortical bone layer. Such engagement may create additional resistance against pullout.

The operator may then verify that the sleeve 11 is set in the bone hole, by performing a tug on the filament ends 21, 22, and may additionally verify that the filament 20 can still slide through the sleeve 11 by pulling on one of the ends 21, 22. The filament 20 should still be slidable through sleeve 11, even when the sleeve is compressed, in order to perform manipulation of the filament 20 in order to, for example, gather and/or pierce tissue to thereby secure tissue to, or adjacent to, the implantation site. For example, such ability to manipulate the filament after deployment of the sleeve is important in rotator cuff surgery as the filament must be manipulable to properly reattach the cuff tissue back to or adjacent to the implantation site.

Alternatively, when tensioning the filament ends 21, 22, rather than pulling both ends simultaneously until the device is completely deployed, the operator, while holding both ends to prevent sliding of the filament, may instead pull on the ends sequentially, such that first, one of the ends 21 or 22 is pulled, and subsequently, the other of the ends 22 or 21 is pulled, to deploy the device.

In another alternative, where the filament includes indicating markers 17a-d, the operator may use such markers as a guide in confirming proper deployment has occurred. As illustrated in FIGS. 1 and 2, markers 17a-d are initially positioned along the length of the sleeve, prior to deployment. As the filament ends 21,22 are pulled, to deploy the device, the markers 17a-d are pulled proximally, towards the operator, along with the filament ends. As illustrated, the sleeve 11 may also migrate proximally during this step. As the proximal markers 17a, 17d pass above the cortical bone 50, they may indicate to the operator that the device has properly deployed. The operator may continue to pull on the ends of the filament until fully deployed (e.g., the filament does not move proximally any further using typical pulling force on the filament ends). However, upon this subsequent pulling, if the distal markers 17b, 17c are exposed above the cortical bone surface 50, then they may indicate that the implant is very close to being pulled out of the bone and the operator should decide if the resistance they feel is adequate or if they would prefer to pull the implant out completely and attempt the procedure again.

In any event, as the filament ends are pulled and the device is deployed, the sleeve resists pullout from the bore hole due to the friction against the cancellous bone 52 surrounding bone hole 51, and such friction is increased as the sleeve is compressed further, as well as if the sleeve migrates proximally (and particularly if the sleeve contacts the underside of the cortical bone layer). Moreover, as the sleeve is compressed, the forces applied to the sleeve may also be transferred to the surrounding cancellous bone, as illustrated in FIGS. 3B-C. Such affect on the cancellous bone may create additional friction and thus anchorage for the sleeve in the bone hole, to resist potential pullout. Further, as the device compresses and further engages the walls of bone hole 51, the surrounding cancellous bone 52 may interdigitate with at least a portion of the sleeve to provide added anchorage of the device within the bone hole. Such interdigitation may include, for example, cancellous bone protrusions overlapping and/or passing between the filaments of the sleeve to engage the sleeve. Moreover, the compressed sleeve, as discussed above, may migrate and engage the underside of the cortical surface, and may through such migration compress even further, and in this more compressed shape will result in a very strong structure to resist being pulled out the small hole in the cortical bone, as illustrated in FIG. 3C.

In another alternative of this method, the insertion tool 30 may also remain within the bone hole during deployment (not shown), to assist in maintaining the sleeve within the bone hole as the filament ends are pulled and the sleeve is compressed.

Following deployment of the device 10, with the sleeve 11 and filament 20 fixedly secured within the bone hole, the device may achieve pullout strengths comparable to traditional metal and polymeric devices despite this device 10 being constructed solely of suture or like filament material. For example, the embodiment of FIGS. 1-4, utilizing #2 suture in a foam block, achieved pullout strengths of at least 60 lbf, though higher pullout strengths are likely depending on the strength of the underlying bone, the diameter of filament 20, and other such variables. Similarly, using the embodiment of FIGS. 1-4, with the addition of a second filament 20, of #2 suture, woven through sleeve 11, a pullout strength of at least 65 lbf was recorded prior to the test foam block fracturing.

In accordance with this embodiment of a method of use, the sleeve 11 is anchored in bone, thus securing the filament 20 to the bone, while still allowing the filament to be slidable through the sleeve. Such ability to maintain the filament in a sliding association to the sleeve, even after the sleeve has been compressed, is important in shoulder and hip surgery, among other surgeries, because the operator may require an adjustable suture length to secure soft tissue at the repair site adjacent to the hole in the bone. This is especially important in arthroscopic surgery because sliding knots are frequently used to secure tissue that is accessed through a cannula. Such sliding association is maintained at least in part by the setup of the filament relative to the sleeve in that the filament passes through the sleeve only once and in a single direction. For example, the filament enters from one end of the sleeve, passes in and out of the plurality of openings in sequential order along the length of the sleeve, and then exits out the second end of the sleeve. Thus, as the sleeve compresses to form a W-shape, as in FIG. 2, the various openings in the sleeve tend to align adjacent one another such that the filament maintains, substantially, a U-shape, and thus can slide through the ends and the openings along the length of the sleeve regardless of the shape of the sleeve.

In one example of the device 10 of FIGS. 1-4, the force required to slide the suture through the deployed sleeve was measured, following a deployment force, applied by tensioning of the ends of the filament, of about 12 lbs. Once the sleeve was deployed (e.g., in the W-shape), between about 1.75-2.75 lbf was required to slide the filament through the sleeve. Of course, alternative embodiments of filaments and sleeves may result in different sliding forces needed to manipulate the filament through the sleeve.

The present invention may also be used, in another embodiment, in a method of securing a tissue to a bone. After the filament has been tensioned and the sleeve anchored in the bone, as in the above embodiment of the method of securing a filament to bone, the filament may then be used to secure tissue to a reattachment site located on the bone at or adjacent to the bone hole. In one embodiment, the filament may be used to reattach rotator cuff tissue, and thus the filament may be manipulated to engage and/or collect the cuff tissue and may be tied or otherwise secured to hold the tissue at the reattachment site. For example, one end 21 or 22 of the filament may be pulled through the tissue (using a needle or the like) and be used to pull the tissue to the reattachment site at or adjacent to the bone hole, at which point the other end of the filament may be incorporated to tie the tissue to the reattachment site, or the like. Other potential tissues on which this method may be used includes at least a portion of a shoulder labrum, at least a portion of a hip labrum, or the like.

In a further embodiment, the fixation device of the present invention may be used in a method of repair of soft tissue, such as a meniscus, ligament or tendon, or the like, wherein such methods do not require that the device 10 be deployed within a bone hole 51. Instead, the device, as to these methods, would function similar to a button anchor for use in, for example, ACL repair, such as is disclosed in U.S. patent application Ser. No. 12/682,324, now U.S. Published App. No. 2011/0125189, filed Oct. 9, 2008 and assigned to the same assignee as this application, the entirety of which is incorporated by reference herein as if fully set forth herein. The device may also serve as a button anchor for use in, for example, meniscus or cartilage repair, such as is disclosed in U.S. patent application Ser. No. 12/550,069, now U.S. Published App. No. 2009/0312792, filed Aug. 28, 2009, the entirety of which is incorporated by reference herein as if fully set forth herein.

In terms of, for example, a ligament or tendon repair, such as an ACL repair, where a tissue graft is secured within a bone tunnel, the device 10 may, following preparation of the bone tunnel by known means, be passed up through the tunnel, using an inserter such as inserter 30. In this embodiment, at least the distal-most portion of the tunnel (e.g., the lateral side of a femur) may have a diameter which allows the undeployed device, as illustrated in FIG. 1, to pass through the tunnel but not the deployed device, as illustrated in FIG. 2. Once the device exits from the bone tunnel, and is thus positioned on the lateral side of the bone (e.g., femur), the filament ends 21,22, which remain outside the opposite end of the bone tunnel, may be pulled to deploy the anchor. The deployment of the anchor may compress the sleeve 11 in a manner, as in FIG. 2, which inhibits the sleeve from passing back through the tunnel. The filament ends may then be tied or otherwise maneuvered to engage the ACL graft, which may then be placed within the bone tunnel as is known in the art. Thus, the device 10 may act as an anchor against which a graft may be tensioned to complete the repair.

In terms of, for example, the repair of a soft tissue tear such as in a meniscus or cartilage mass, where the tear is to be approximated to promote healing of same, the device 10 may be passed through the tissue mass, through the tear, and through a side surface of the tissue. In this embodiment, the inserter 30 may include, for example, a needle tip or other structure capable of forming a pathway through which the device, in the undeployed configuration as in FIG. 1, may pass. Once the device is positioned outside the side surface of the tissue, the filament ends, which remain in position on the opposite side of the tissue, may be pulled to deploy the sleeve 11. Once the sleeve is deployed, the sleeve is thus too wide to fit back through the pathway. The filament ends may then be tied or otherwise maneuvered to approximate the tear, which is positioned between the sleeve and the filament ends. The filament ends may then form a knot, or otherwise secure to one another, against the opposite side of the tissue. Thus, the device 10 may act as an anchor against which the filament ends may be tensioned to approximate the tear in the soft tissue to complete the repair.

Alternatively, these methods may also be used to secure a bone to hard tissue, such as another bone, as in a syndesmosis repair. In such a method, the filament may, as above, pass through the other bone (e.g., through a bone throughhole) or may pass around the other bone to effect a reattachment of the two bones to one another to promote healing of the injured joint. Thus, upon activation of the device, the filament ends may then engage the other bone and be tied together to secure the two bones together. Such methods of use may be utilized in the repair of bone in the ankle joint or in the acromioclavicular joint.

Figure 5:
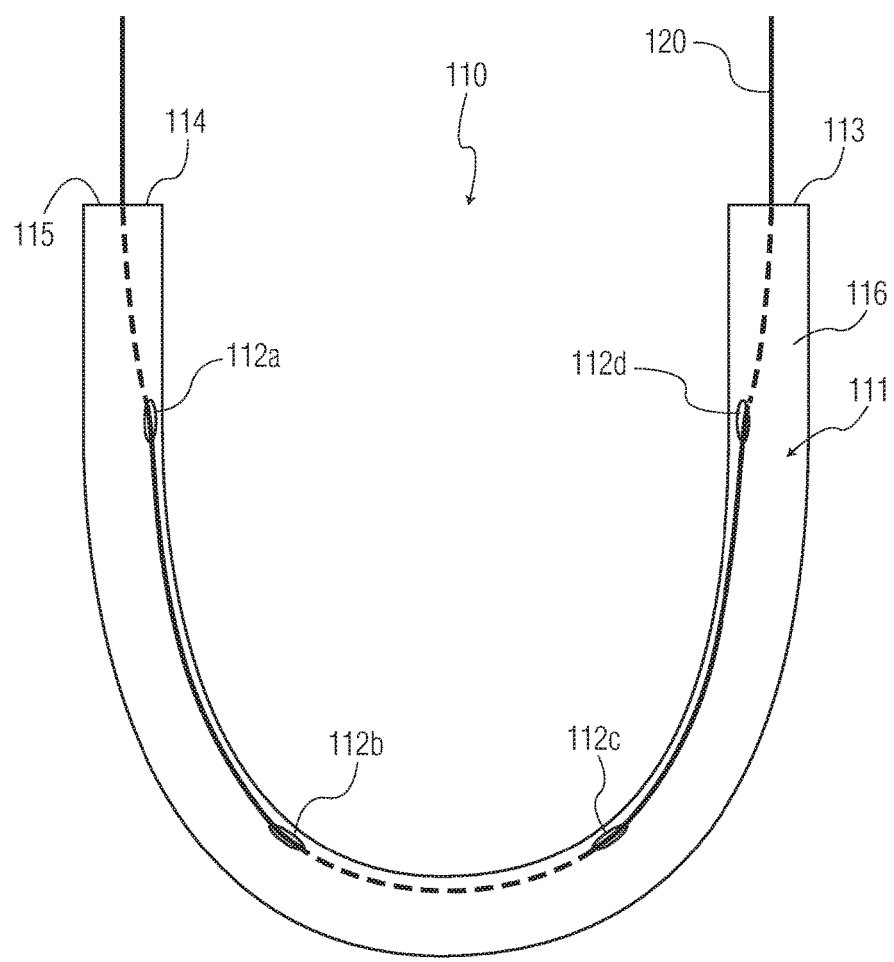
FIG. 5 illustrates another embodiment of a fixation device of the present invention.
Figure 6:
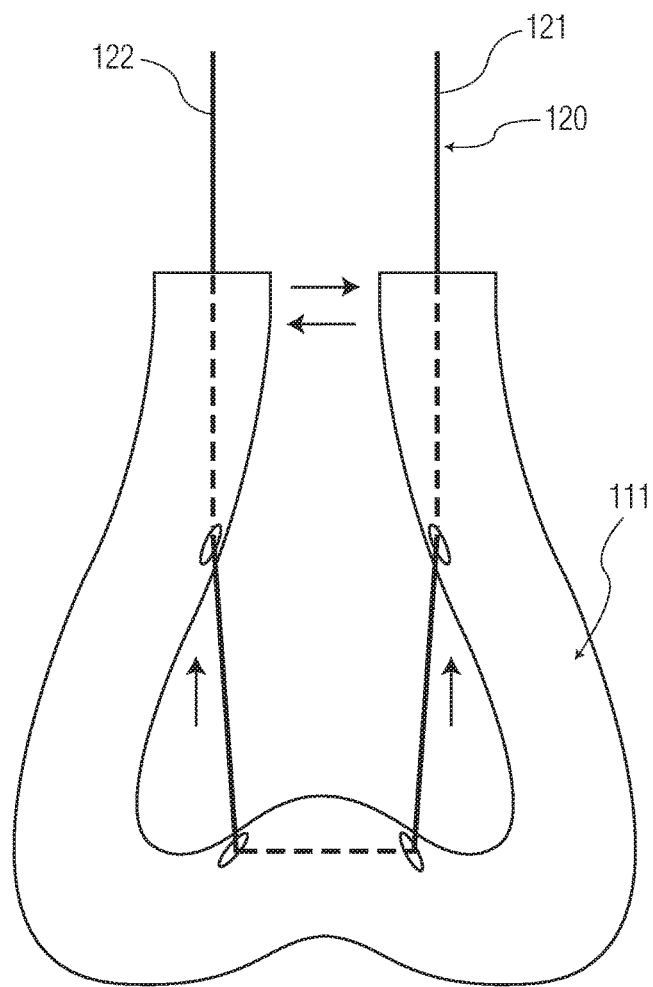
FIG. 6 illustrates the fixation device of FIG. 5 after tensioning the filament 120.

As illustrated in FIGS. 5 and 6, another embodiment of fixation device 110 includes a sleeve member 111 and a filament 120. The sleeve member 111 includes an interior 115 and an exterior surface 116, both of which extend along a length defined between a first end 113 and a second end 114. The sleeve member 111 may be substantially hollow. The exterior surface also includes at least two openings 112b, 112c positioned along the length of the exterior surface 116, each of which form a passageway through the exterior surface and into the interior 115. As illustrated, in this embodiment, the exterior surface may include four openings (for example, 12a, 12b, 12c, 12d), though any other number of openings in any configuration along the length of the exterior surface may be present.

This embodiment also includes a filament 120 having a length and at least a portion of this length is positioned within the interior 115 of sleeve 111. The filament is slidable within the interior 115. The filament may also pass through at least one of the openings 112 along the exterior surface 116 of the sleeve 111. For example, as in FIG. 5, filament 120 may exit the interior 115 through opening 112a re-enter the interior through opening 112b, exit the interior once again through opening 112c, and re-enter the interior through opening 112d.

Comparing FIG. 5 with the first disclosed embodiment, in FIG. 1, it is apparent that the filament 120 remains inside the interior at the bottom portion (between openings 112b and 112c), while the filament 20 is outside of the interior at the similar bottom portion (between openings 12c and 12d) in FIG. 1. In addition to the aforementioned differences in width of the device upon placement on an inserter, these differing configurations may provide different forces on the sleeve as the filament 20, 120 is tensioned to compress the sleeve. For example, in FIG. 1, as the filament 20 is tensioned, openings 12c and 12d may be pulled towards one another such that the sleeve between these openings may be pinched or crushed to form the W-shape. In FIG. 5, however, the tensioning of filament 120 may provide an upward force at openings 112b and 112c, thereby moving the portion of the sleeve between these openings up towards the first and second ends 113, 114 which may form the W-shape. Thus, these two exemplary embodiments illustrate two different relationships of a sleeve and a filament, either of which may result in a compressed sleeve capable of securing a filament within a bone hole.

The fixation device embodiment illustrated in FIGS. 5 and 6 may be used in similar methods of use as illustrated in FIGS. 3 and 4 and as discussed above.

Figure 7A:
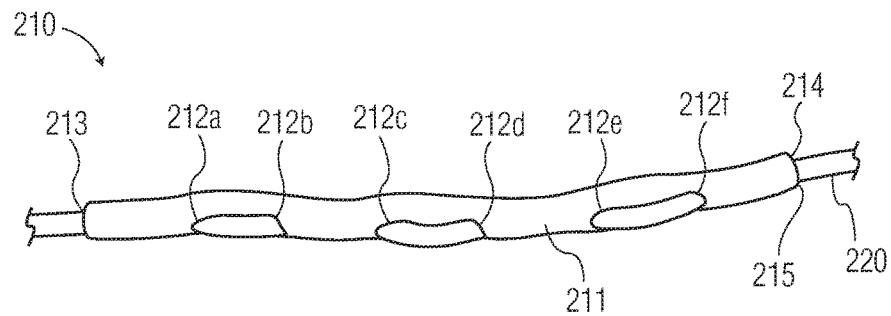
FIGS. 7A-C illustrate a further embodiment of a fixation device of the present invention.
Figure 7B:
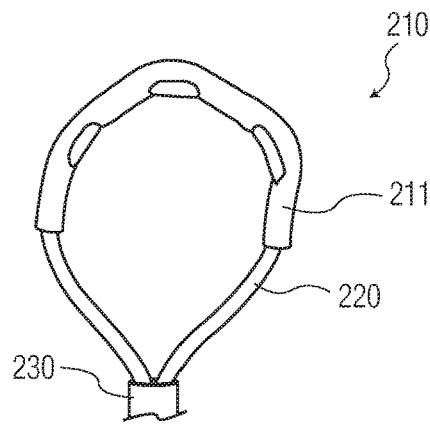
Figure 7C:
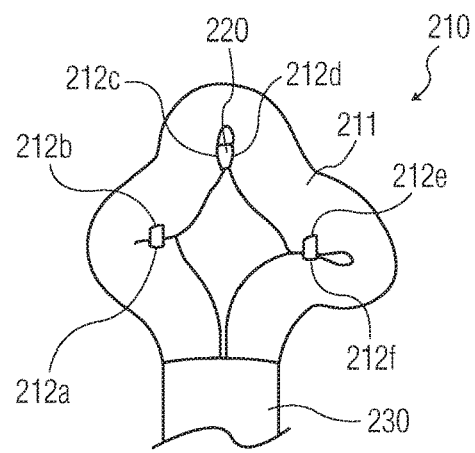

In further alternative embodiments, which also may be used in similar methods of use as illustrated in FIGS. 3 and 4 and as discussed above, the sleeve and filament may have a relationship which results in the sleeve, upon compressing, attaining a compressed shape other than the W-shape discussed above. For example, as illustrated in FIGS. 7A-C, the sleeve 211 may have a U-shaped starting shape (FIG. 7B), but upon compressing, may attain a clover shape (FIG. 7C). Similar to the embodiments discussed in detail above, the openings 212a-f of this embodiment likewise, upon compression, may move towards one another, e.g., opening 212a and opening 212b are adjacent one another, and even contacting one another, upon compression of sleeve 211. Moreover, in this closer shape, the filament 220 may still have a generally U-shaped arrangement, within the clover shape of sleeve 211, such that the filament 220 may still slide within the sleeve 211.

FIGS. 8-16 illustrate other exemplary shapes which the sleeve may attain upon compressing. As illustrated, the various shapes depend on a variety of factors including but not limited to the number of openings along the length of the sleeve, the location of the openings along the sleeve, the relationship of the filament relative to the sleeve, and the shape of the openings on the sleeve. The pullout strength and capability of being used in the above disclosed methods may be similar to the embodiment disclosed in FIGS. 1-4. It should be noted that in all of the embodiments disclosed in this application, particularly those in FIGS. 7-16, upon compression, the sleeve may not always attain the same shape each and every time. For example, the shape and size of the bone hole may force the sleeve into a different shape, upon compression, than those illustrated herein. Also, in another example, the exact dimensions and locations of the openings through the sleeve may be altered slightly which could result in an alternative shape of the sleeve upon its compression.

Figure 8A:
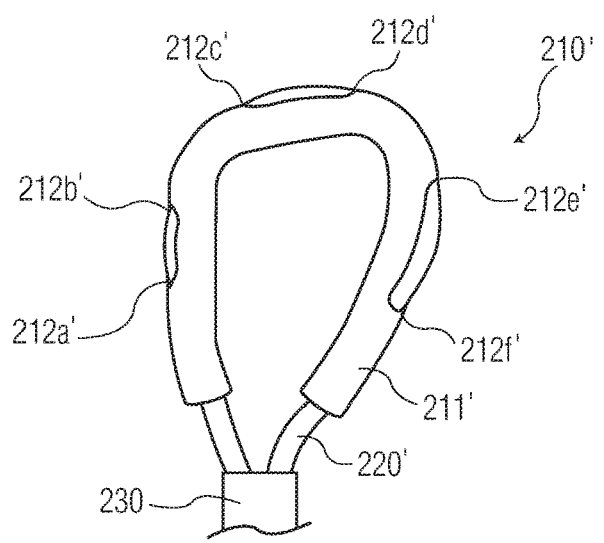
FIGS. 8A-B illustrate an alternative configuration of the fixation device of FIGS. 7A-C.
Figure 8B:
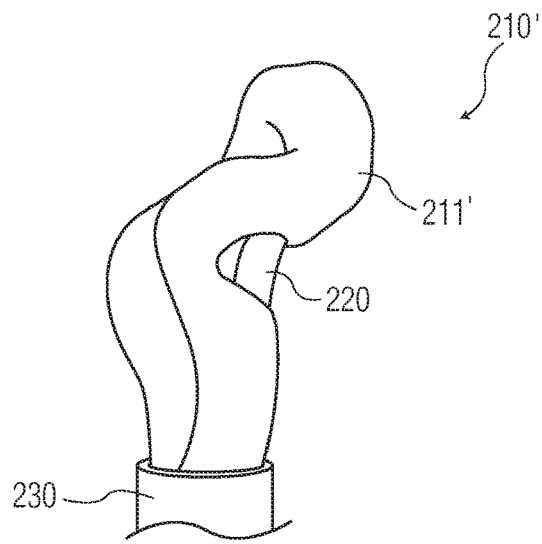

For example, in FIGS. 8A-B, the relationship of the sleeve 211' and filament 220' is the same as the relationship illustrated in FIG. 7A, except that when the device 210' is curved into the U-shape of FIG. 8A, the filament 220' exits outside the sleeve 211' on the outside of the U-shape, e.g., between openings 212a' and 212b'. By contrast, the filament 220 illustrated in FIG. 7B, upon exiting the sleeve 211, exits on the inside of the U-shape, e.g., between openings 212a and 212b. While FIGS. 7B and 8A appear to be quite similar, the two different relationships may result in drastic differences once the sleeves are compressed, as illustrated in FIGS. 7C and 8B, which illustrate alternative shapes of compressed sleeves.

Figure 9A:
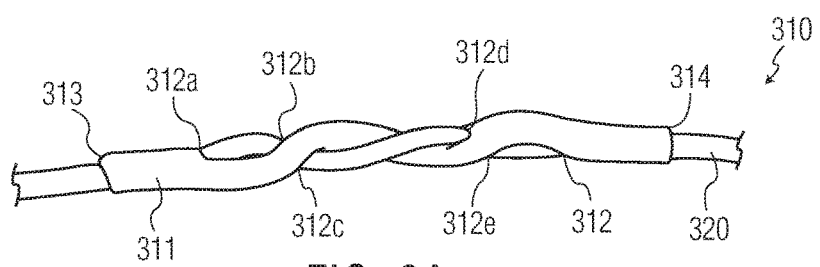
FIGS. 9A-C illustrate yet another embodiment of a fixation device of the present invention.
Figure 9B:
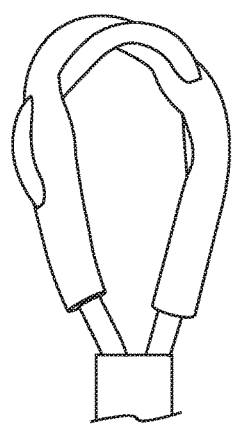
Figure 9C:
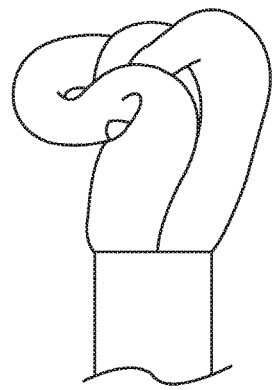
Figure 10A:
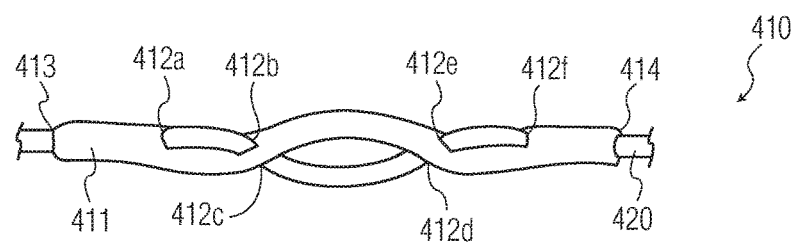
FIGS. 10A-C illustrate another embodiment of a fixation device of the present invention.
Figure 10B:
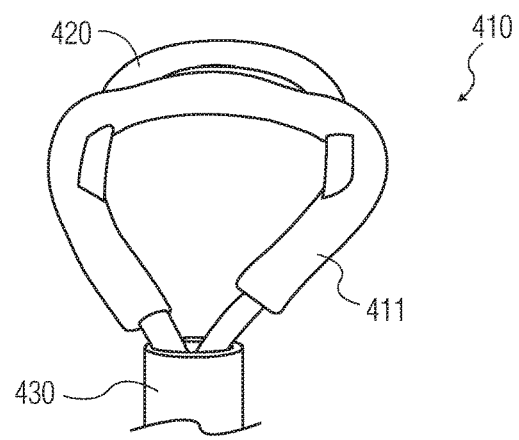
Figure 10C:
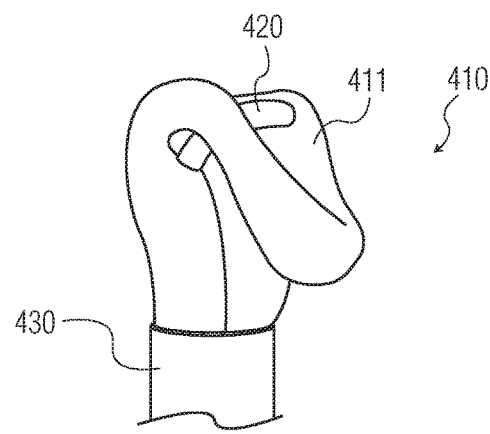
Figure 11A:
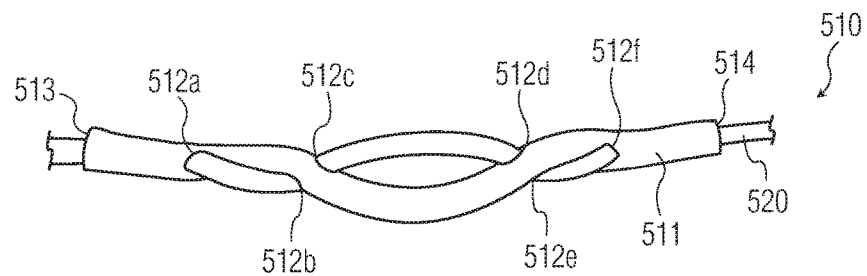
FIGS. 11A-C illustrate a further embodiment of a fixation device of the present invention.
Figure 11B:
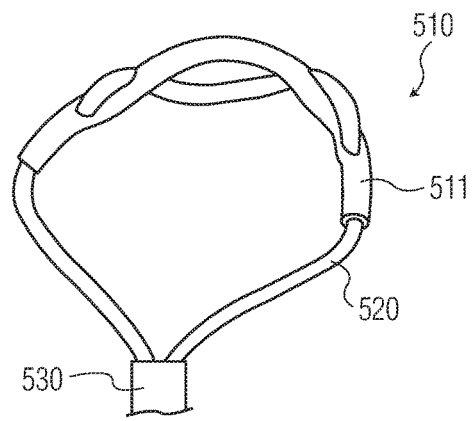
Figure 11C:
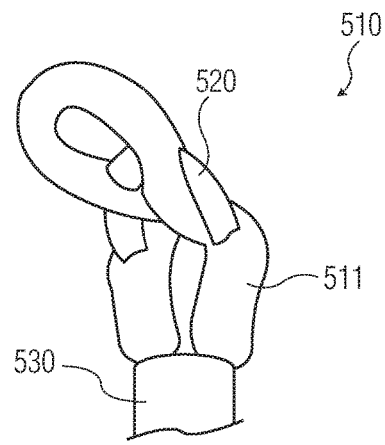
Figure 12A:
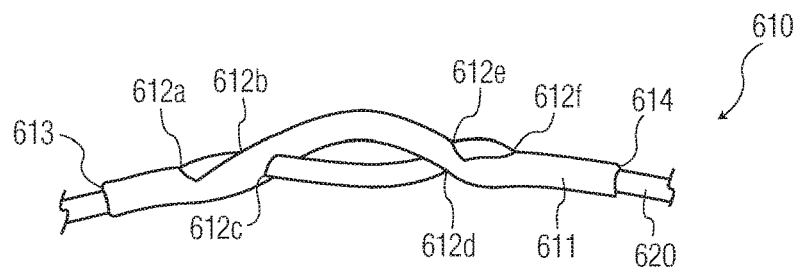
FIGS. 12A-C illustrate an additional embodiment of a fixation device of the present invention.
Figure 12B:
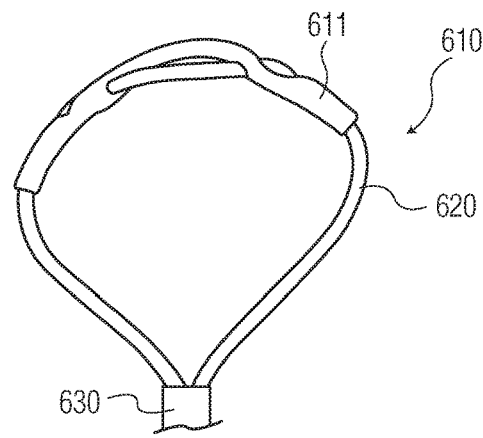
Figure 12C:
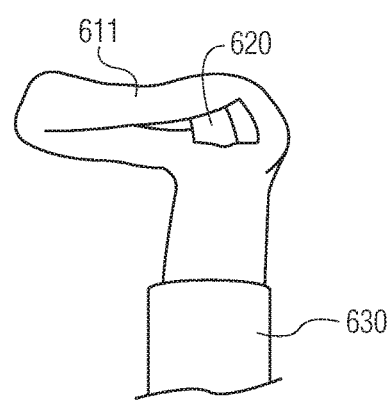

In yet another example of such differences, FIGS. 9A-C illustrate another alternative embodiment of a relationship of a sleeve 311 and a filament 320 forming an device 310. In this embodiment, openings 312a and 312b are radially offset from one another, and the filament 320 must be twisted around the outside of the sleeve to reach between opening 312a and opening 312b. Upon folding of the sleeve 311 (FIG. 9B), the openings 312a and 312b remain radially offset to one another, and filament 320 twists around sleeve 311 such that it may pass through the openings 312a and 312b. Such a relationship may result in yet another alternative shape of the sleeve upon compressing during deployment of the sleeve. Again, it should be observed, that the filament, upon compression of the sleeve, substantially maintains a U-shape, within and around the sleeve, such that sliding of the filament remains possible.

In some embodiments, as in FIGS. 1-8, the filament, when positioned within the interior of the sleeve, may extend in a generally longitudinal path along the length of the sleeve such that the filament and sleeve are substantially parallel with one another. Using FIG. 7A as an example, filament 220 is generally positioned axially along the length of the sleeve 211 while entering and exiting the interior of the sleeve via openings 212 which are positioned along the length of sleeve 211 and generally in series—one after the other—along the length.

In an alternative example, however, the filament may be generally transverse to the interior of the sleeve, when the filament is positioned within the interior. For example, such a relationship is variously illustrated in FIGS. 9-16. As illustrated clearly in FIGS. 14A-C, for example, the filament may pass through opening 812b, travel transversely through the interior, and out opening 812c. Such a relationship of the filament and sleeve is also shown as to openings 812d and 812e, and 812f and 812g. As shown, however, the filament may still remain substantially parallel to the interior of the sleeve at the ends of the sleeve, e.g., between end 813 and opening 812a and end 814 and opening 812h, such that the filament exits from the interior at the first and second ends. This is similar to other embodiments herein. Such a relationship may provide for better sliding of the filament through the sleeve.

Such embodiments having a generally transverse configuration when the filament passes through the sleeve as FIGS. 9-16 may result in alternative shapes of the sleeve when compressed. As in the other embodiments described above, the shape of the sleeve when compressed will depend on the number of openings along the length of the sleeve, the location of the openings along the sleeve, the relationship of the filament relative to the sleeve, and the shape of the openings on the sleeve.

Figure 13A:
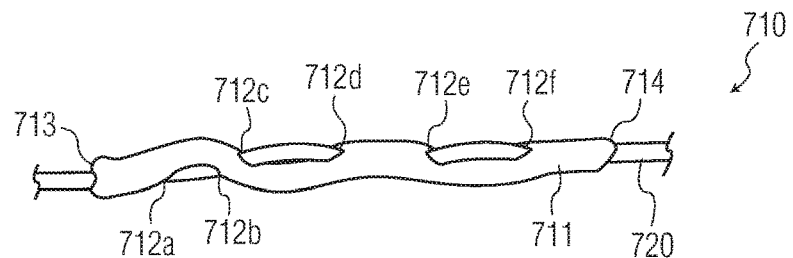
FIGS. 13A-C illustrate yet another embodiment of a fixation device of the present invention.
Figure 13B:
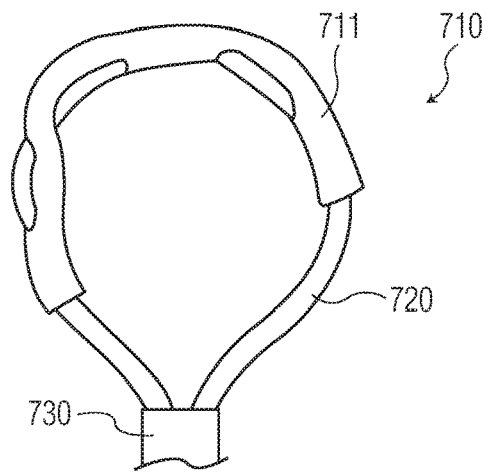
Figure 13C:
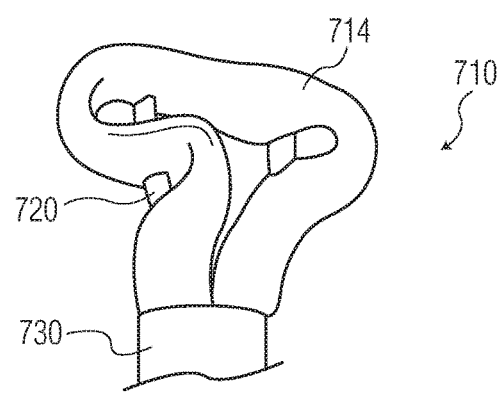

In yet another alternative, the filament and sleeve may be in a hybrid configuration whereby the filament, along at least a first portion of its length other than at the ends of the sleeve, is substantially parallel to the interior of the sleeve, and along at least one other portion, may be generally transverse to the interior of the sleeve. Such variations are illustrated in FIGS. 13A-C. Thus, in this type of relationship, the filament is again generally parallel to the sleeve at the ends of the sleeve (between end 713 and opening 712a and end 714 and opening 712f). The filament and sleeve are also generally parallel between opening 712c through openings 712d and 712e and on to opening 712f and end 714. The filament is transverse to the sleeve from opening 712b to 712c.

The various embodiments illustrated in the figures provide many examples of the device of the present invention. While the relationship between the filament and sleeve varies from embodiment to embodiment, each of the embodiments have similarities such as, for example: the filament and sleeve are generally parallel to one another at the ends of the sleeve such that the filament exits from the ends of the sleeve; the sleeve and filament can be moved to a U-shape, prior to deployment of the device, and loaded onto an inserter; and with the sleeve compressed, the filament generally maintains a U-shape such that it may remain slidable through the sleeve even when the sleeve is compressed.

These various embodiments result in a smaller device than those presently in public use because the filament only passes through the interior of the sleeve once along its length, remains within the sleeve and exiting through the ends of the sleeve, and, in many embodiments, is outside the sleeve at the location where the inserter tip holds the device, resulting in a generally smaller diameter of the device. The smaller sized device allows for a smaller hole to be prepared in the bone, and a smaller access port to the bone, which results in a smaller surgical site in the patient.

Moreover, in the event the device does pull out from the bone post-surgery, since the device is made entirely of a filament-like material, such as suture, the device would not lacerate adjacent anatomy within the patient, which is a concern if a traditional device pulls out from the bone.

The present invention may also include various kits and systems which include at least one of the device embodiments above. For example, in one embodiment, the present invention may include a system including a device, including a sleeve and filament, and an inserter. The system may be packaged individually, and even sold separately, such that the surgeon may place the device on the inserter. Alternatively, the device may come pre-installed on the inserter, within a single package, such that the surgeon may remove the system from the packaging and immediately use the system and install the device within a bone hole.

In another embodiment, such a system may further include the aforementioned drill guide and drill, which may come pre-packaged as an entire system or which may be sold separately and later combined by the surgeon and used for the above discussed methods of use.

In another embodiment, the present invention may include a kit which includes a plurality of devices, each having a sleeve and filament, and an inserter. The plurality of devices may be any combination of the above devices. For example, the plurality of devices may include more than one of the device disclosed in FIGS. 1-4, wherein the sleeve of each device has a different diameter and/or length than the other sleeves of the other devices. Alternatively, the sleeve of each device may have a different number and/or positioning of openings, such that the appropriate device may be selected which will provide the desired pullout strength or compression properties (which may be dependent on the anatomy in which the device is implanted, the condition of the bone in which the device is implanted, or the like). Alternatively, the plurality of devices may include various devices of the above embodiments, or other similar devices, from which a surgeon may select from based on the specifics of the surgical site, pullout strength required, and the like.

Such kits may further include a plurality of drill bits which may be matched with a device, selected from the plurality of devices, to prepare an appropriately sized bone hole for insertion of the device.

Any other suitable combination is also envisioned for the above systems and kits which may be useful or desirable to a surgeon. For example, the various components of the systems or kits may all be available to a surgeon a la carte, such that a unique system or kit may be created for a particular surgeon dependent on the needs or desires of the particular surgeon.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A filamentary fixation system, comprising:
    a sleeve formed of filamentary material having a longitudinal lumen defined through a length of the sleeve and between a first open end and a second open end, the sleeve defining first and second openings positioned along the length between the first open end and the second open end, the sleeve having a coating adapted to allow for tissue ingrowth; and
    a filament formed of filamentary material including a first free end and a second free end, the filament extending through the first open end and being disposed inside the sleeve from the first open end to the first opening, at least a portion of the filament being disposed outside the sleeve between the first opening and the second opening, the filament being disposed inside the sleeve from the second opening to the second open end, and the filament extending through the second open end, wherein the filament does not overlap itself within the interior of the sleeve.

2. The system of claim 1, wherein the coating comprises hydroxyapatite powder, tricalcium phosphate, collagen-based additives, platelet-rich plasma, or bioactive glass.

3. The system of claim 2, wherein the coating is positioned on an exterior surface of the sleeve.

4. The system of claim 1, wherein an interior surface of the sleeve defines a hollow volume.

5. The system of claim 4, wherein the sleeve further comprises a longitudinal axis extending through the hollow volume, the first open end and the second open end.

6. The system of claim 1, wherein the sleeve is pliable and is expandable or compressible.

7. The system of claim 6, wherein the filament is adapted to be slidable through the sleeve when the sleeve is expanded and compressed.

8. The system of claim 1, wherein the sleeve further includes a third opening and a fourth opening, and at least a portion of the filament is disposed inside the interior from the first open end to the first opening, outside the sleeve from the first opening to the second opening, inside the sleeve from the second opening to a third opening, outside the sleeve from the third opening to the fourth opening, and inside the sleeve from the fourth opening to the second open end of the sleeve.

9. The system of claim 1, wherein the filament further includes an at least one indicating marker along its length.

10. A filamentary fixation system, comprising:
    a sleeve formed of filamentary material having a longitudinal lumen defined through a length of the sleeve and between a first open end and a second open end, the sleeve defining first and second openings along the length between the first open end and the second open end, the sleeve having a coating adapted to allow for tissue ingrowth; and
    a filament including a first free end and a second free end, and a length therebetween, the filament extending through the first open end and being disposed inside the sleeve from the first open end to the first opening, at least a portion of the filament being disposed outside the sleeve between the first opening and the second opening, the filament being disposed inside the sleeve from the second opening to the second open end, and the filament extending through the second open end, wherein the filament does not overlap itself within the sleeve and is adapted to be slidable through the sleeve.

11. The system of claim 10, wherein the filament is formed of filamentary material.

12. The system of claim 10, wherein the sleeve is pliable and is expandable or compressible, and the filament is adapted to be slidable through the sleeve when the sleeve is expanded or compressed.

13. The system of claim 10, wherein the coating comprises hydroxyapatite powder, tricalcium phosphate, collagen-based additives, platelet-rich plasma, or bioactive glass.

14. The system of claim 13, wherein the coating is positioned on an exterior surface of the sleeve.

15. The system of claim 10, wherein the filament further includes at least one indicating marker along its length.

16. A method for securing a filament in a hole in a bone, comprising the steps of:
    accessing the bone and preparing a bone hole;
    inserting a fixation device into the bone hole, the device including:
        a sleeve formed of filamentary material having a longitudinal lumen defined through a length of the sleeve and between a first open end and a second open end, the sleeve defining first and second openings positioned along the length between the first open end and the second open end, the sleeve having a coating adapted to allow for tissue ingrowth; and
        a filament formed of filamentary material including a first free end and a second free end, the filament extending through the first open end and being disposed inside the interior from the first open end to the first opening, at least a portion of the filament being disposed outside the sleeve between the first opening and the second opening, the filament being disposed inside the sleeve from the second opening to the second open end, and the filament extending through the second open end, wherein the filament does not overlap itself within the interior of the sleeve; and
    compressing the sleeve member within the bone hole.

17. The method of claim 16, wherein the compressing step comprises pulling the first and second free ends of the filament.

18. The method of claim 16, further comprising, after the compressing step, adjusting the filament by pulling on one of the two ends of the filament to slide the filament through the sleeve.

19. The method of claim 16, wherein the compressing step alters the shape of the sleeve from a substantially U-shape to a substantially W-shape.

* * * * *